(12) United States Patent
Felden et al.

(10) Patent No.: US 9,765,332 B2
(45) Date of Patent: Sep. 19, 2017

(54) OLIGONUCLEOTIDES AND METHODS FOR INHIBITING OR REDUCING BACTERIAL BIOFILMS

(71) Applicants: INSERM (Institute National de la Sante et de la Recherche Medicale), Paris (FR); Universite de Rennes 1, Rennes (FR)

(72) Inventors: Brice Felden, Rennes Cedex (FR); Valerie Bordeau, Rennes Cedex (FR)

(73) Assignees: INSERM (INSTITUT NATIONAL DE LA SANTE ET DE LA RECHERCHE MEDICALE), Paris (FR); UNIVERSITE DE RENNES 1, Rennes (FR)

( * ) Notice: Subject to any disclaimer, the term of this patent is extended or adjusted under 35 U.S.C. 154(b) by 0 days.

(21) Appl. No.: 15/113,988

(22) PCT Filed: Jan. 29, 2015

(86) PCT No.: PCT/IB2015/000212
§ 371 (c)(1),
(2) Date: Jul. 25, 2016

(87) PCT Pub. No.: WO2015/118407
PCT Pub. Date: Aug. 13, 2015

(65) Prior Publication Data
US 2016/0348102 A1    Dec. 1, 2016

Related U.S. Application Data

(60) Provisional application No. 61/933,025, filed on Jan. 29, 2014.

(51) Int. Cl.
C12N 15/113   (2010.01)
C12N 15/115   (2010.01)

(52) U.S. Cl.
CPC .......... *C12N 15/113* (2013.01); *C12N 15/115* (2013.01); *C12N 2310/11* (2013.01); *C12N 2310/14* (2013.01); *C12N 2310/141* (2013.01); *C12N 2310/16* (2013.01)

(58) Field of Classification Search
None
See application file for complete search history.

(56) References Cited

U.S. PATENT DOCUMENTS

| 6,365,401 B1 * | 4/2002 | Mahan | C07K 14/255 |
| | | | 435/320.1 |
| 2006/0003322 A1 * | 1/2006 | Bentwich | C12N 15/113 |
| | | | 435/6.16 |

OTHER PUBLICATIONS

Holmqvist et al.; "Two antisense RNAs target the transcriptional regulator CsgD to inhibit curli syntheses"; The EMBO Journal, vol. 29, No. 11, Jun. 2, 2010, pp. 1840-1850.
Hu et al.; "Inhibition of biofilm formation by the antisense peptide nucleic acids targeted at the motA gene in Pseudomonas aeruginosa PAO1 strain"; World Journal of Microbiology and Biotechnology, vol. 27, No. 9, Jan. 19, 2011, pp. 1981-1987.
Hall-Stoodley et al.; "Bacterial Biofilms: From the Natural Environment to Infectious Diseases"; Nature Reviews/Microbiology, vol. 2, No. 2, Feb. 1, 2004, pp. 95-108.

* cited by examiner

Primary Examiner — Tracy Vivlemore
(74) Attorney, Agent, or Firm — Whitham, Curtis & Cook, P.C.

(57) ABSTRACT

The present invention relates to oligonucleotides useful for inhibiting or reducing bacterial biofilms.

11 Claims, 13 Drawing Sheets

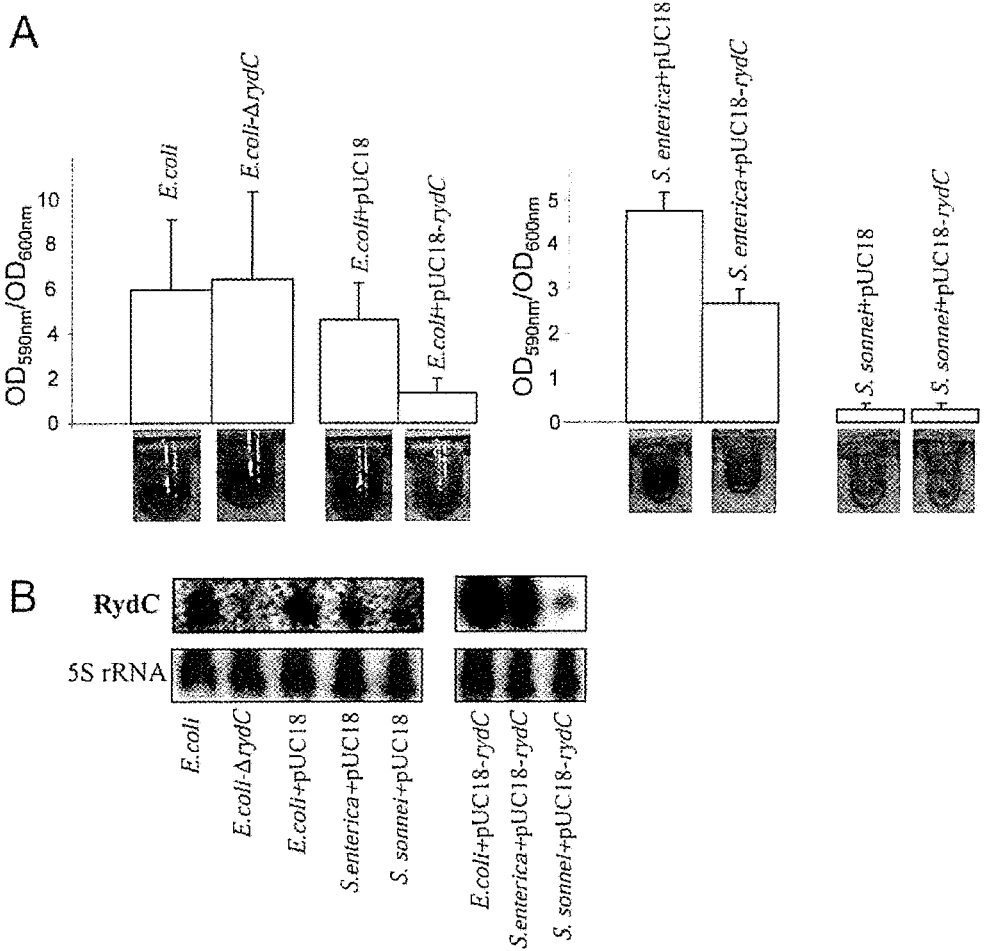
Figure 1 A and B

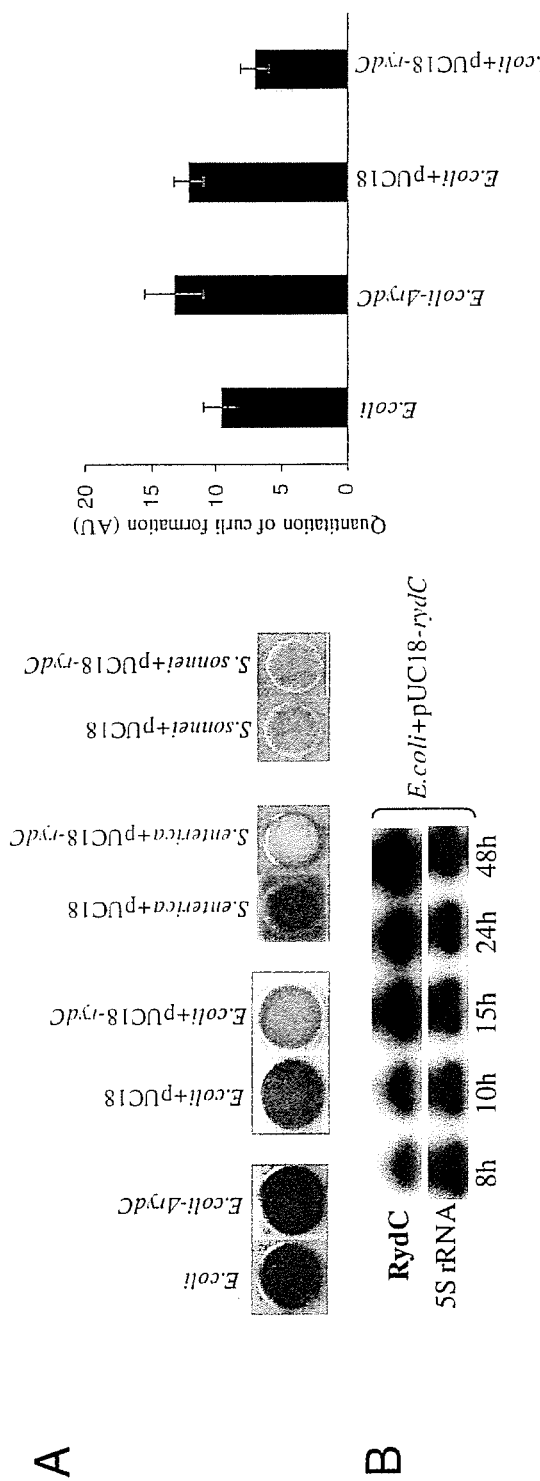
Figure 2 A and B

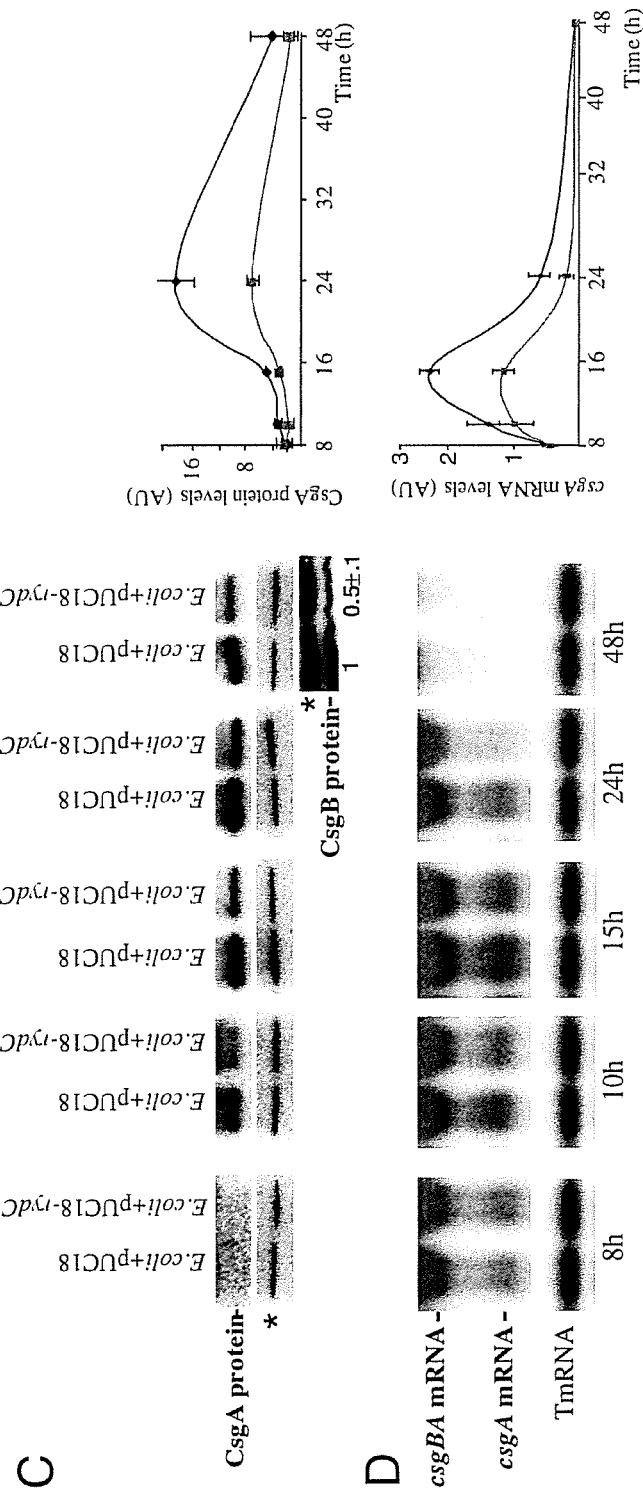
Figure 2 C and D

Figure 3:
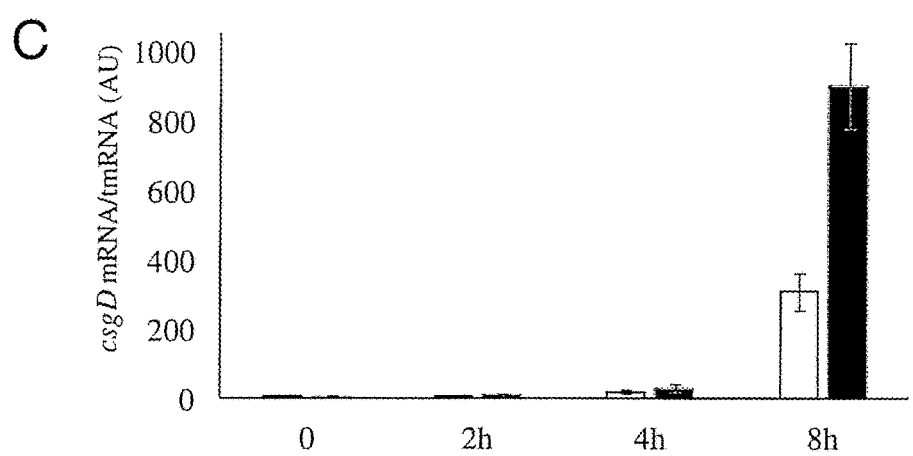

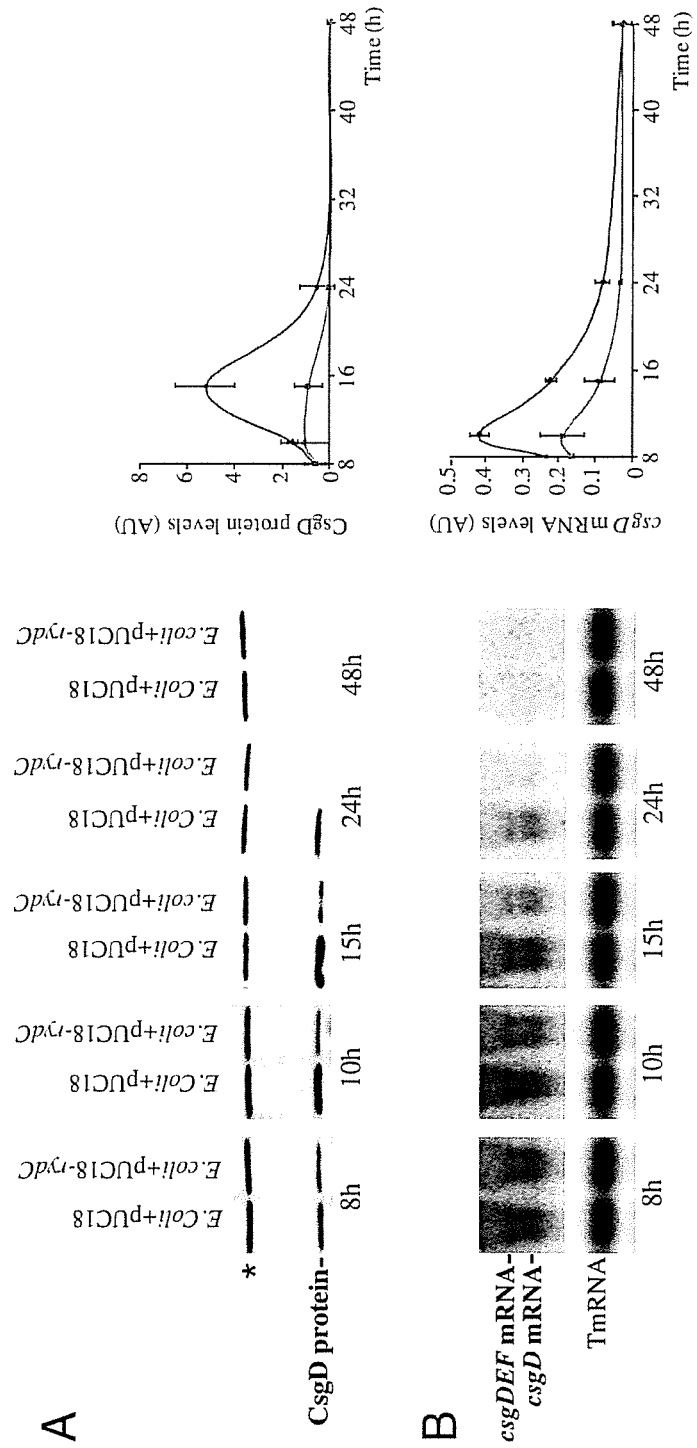
Figure 3 A and B

Figure 4:
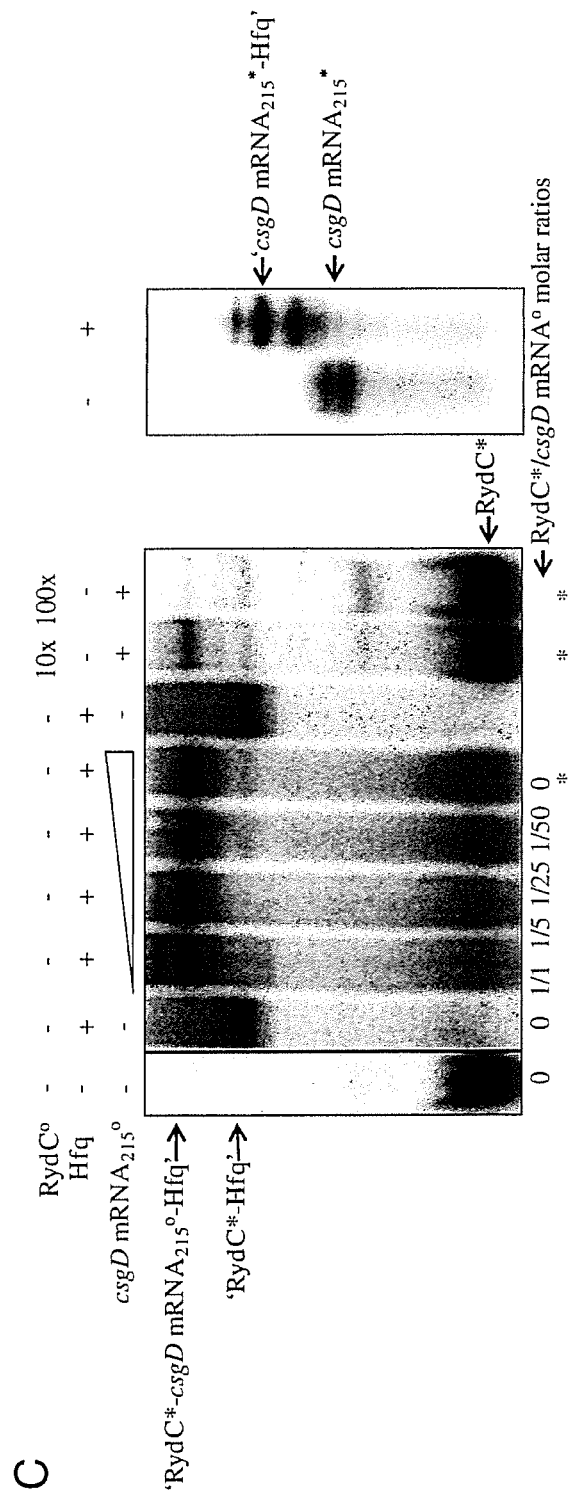

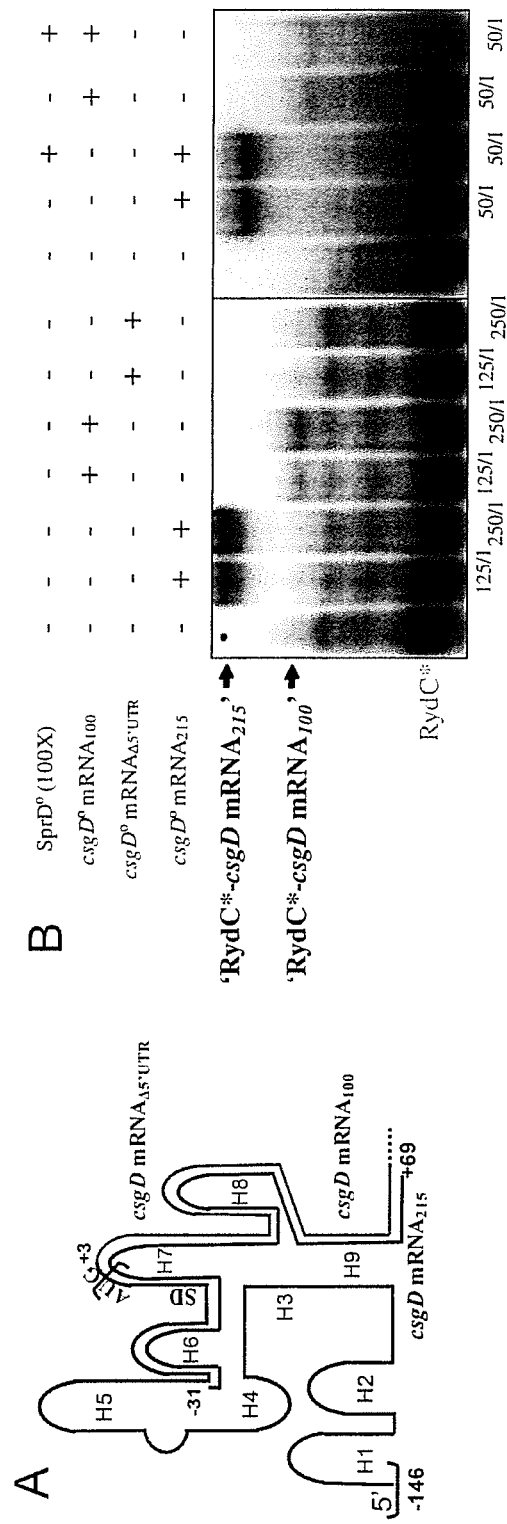
Figure 4 A and B

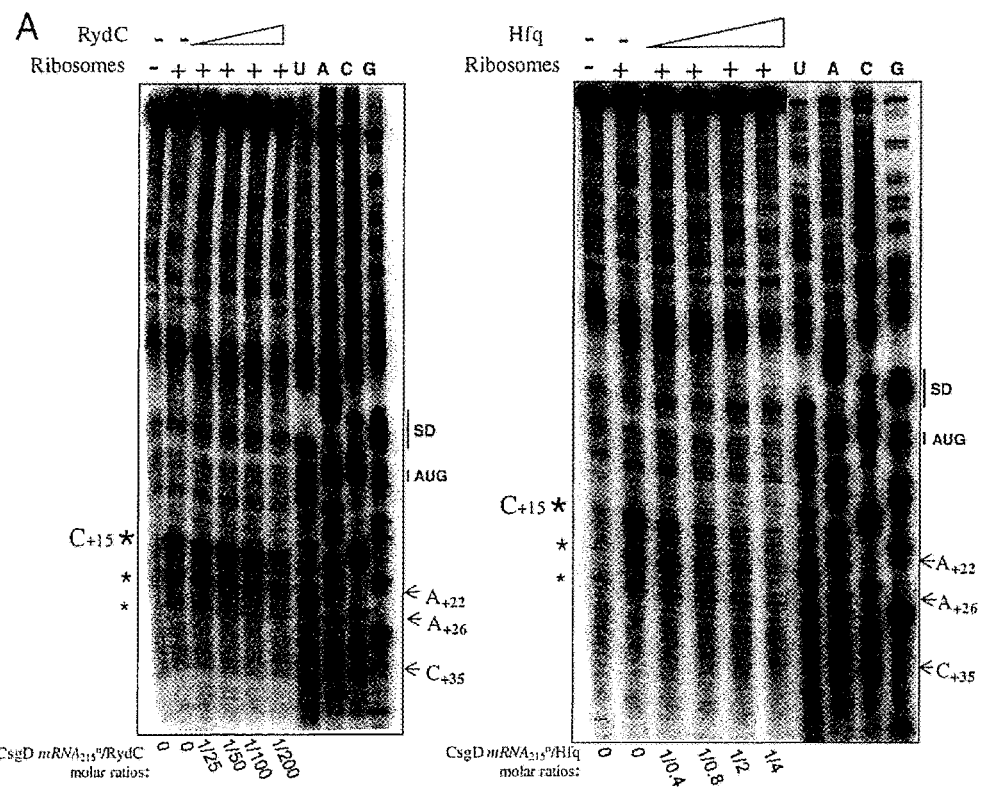
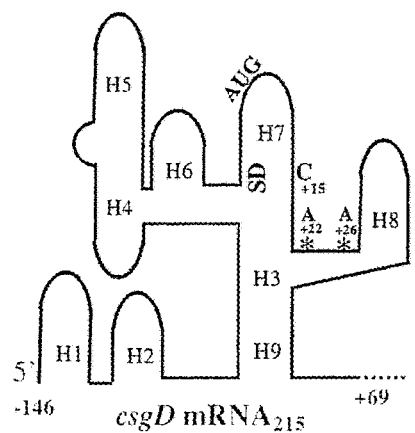
Figure 5 A and B

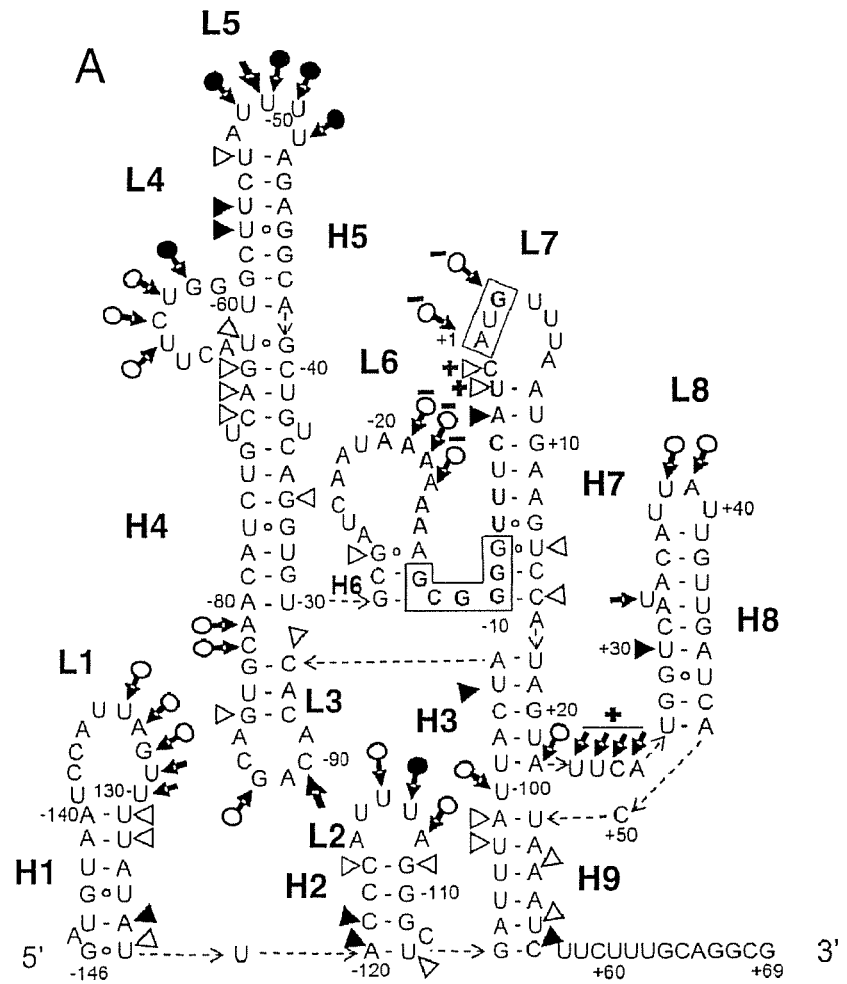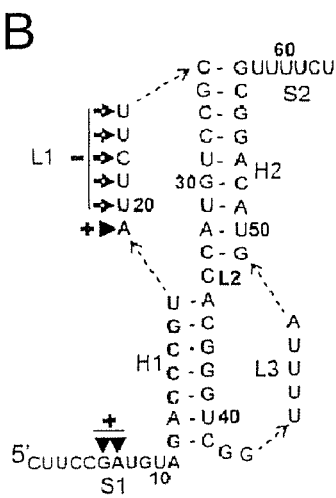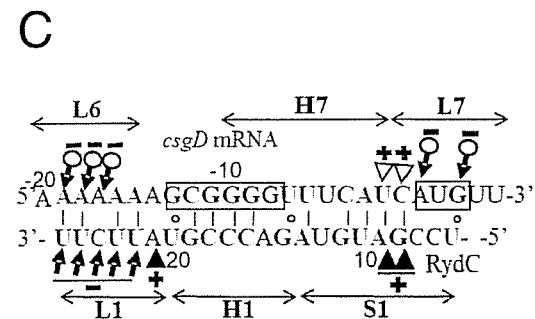
Figure 6 A, B and C

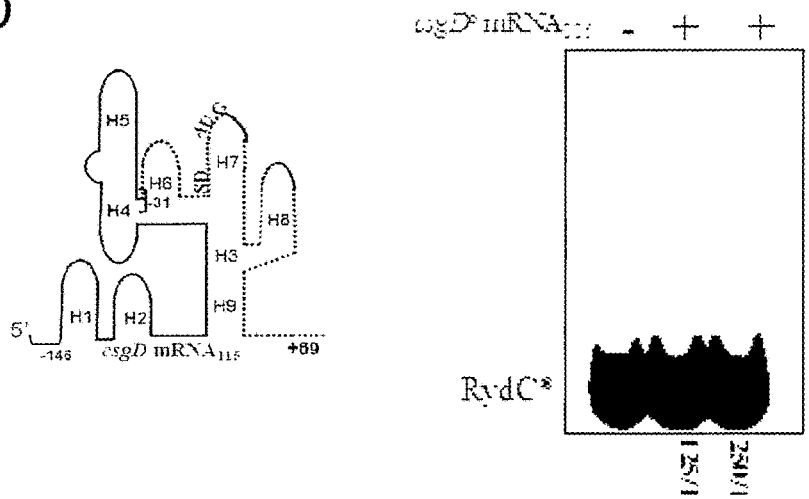
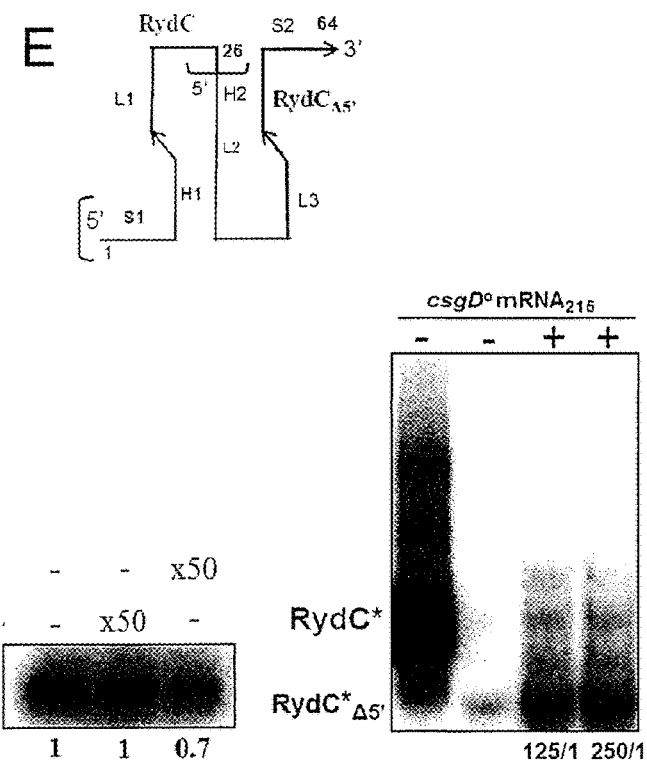
Figure 6 D and E

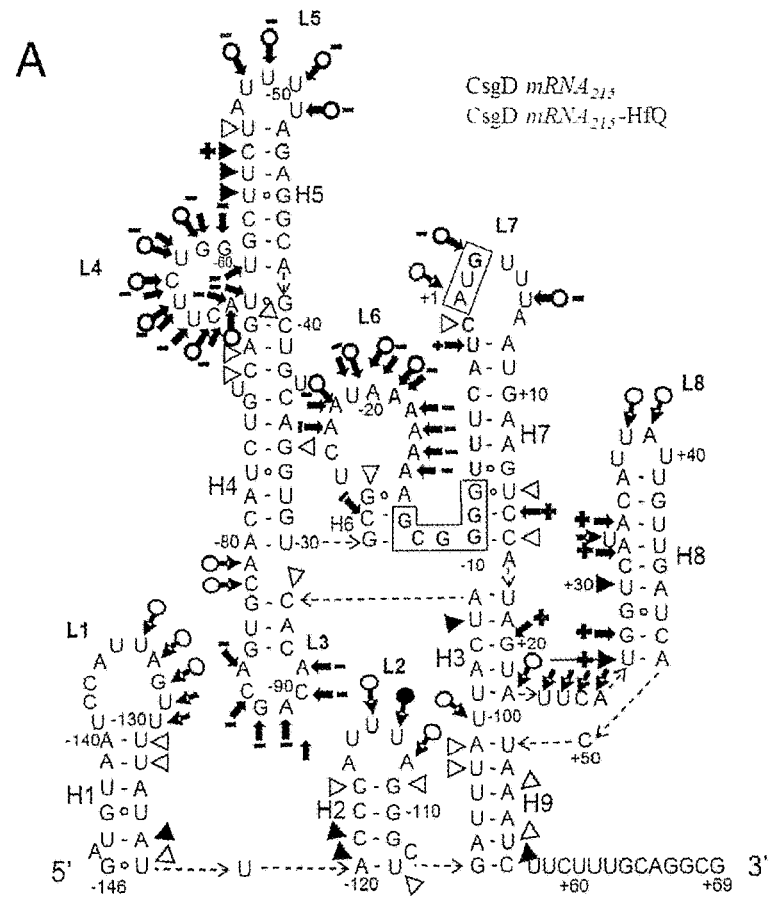
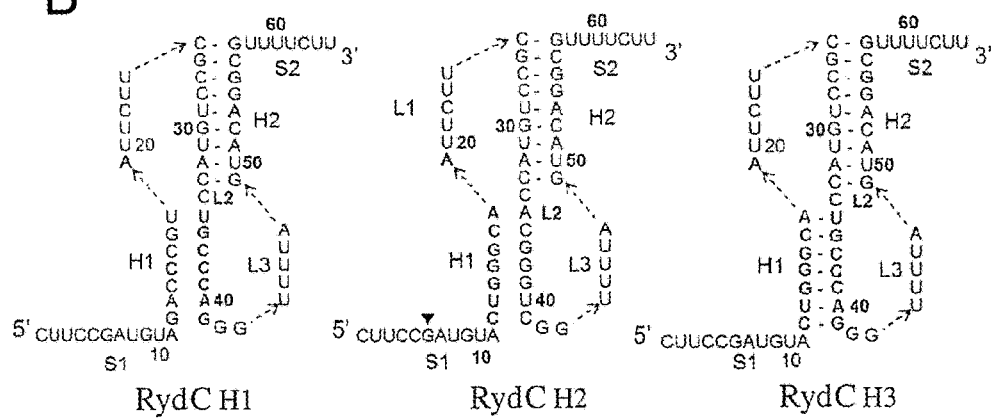
Figure 7 A and B

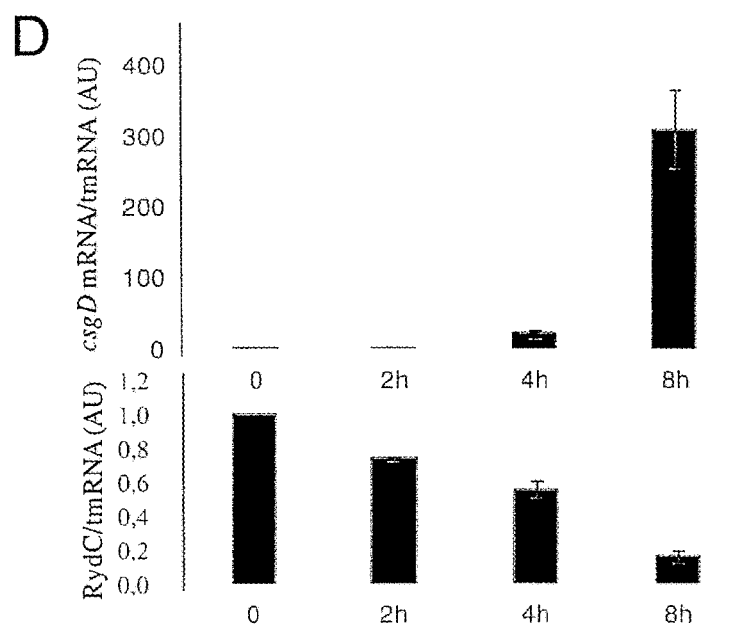
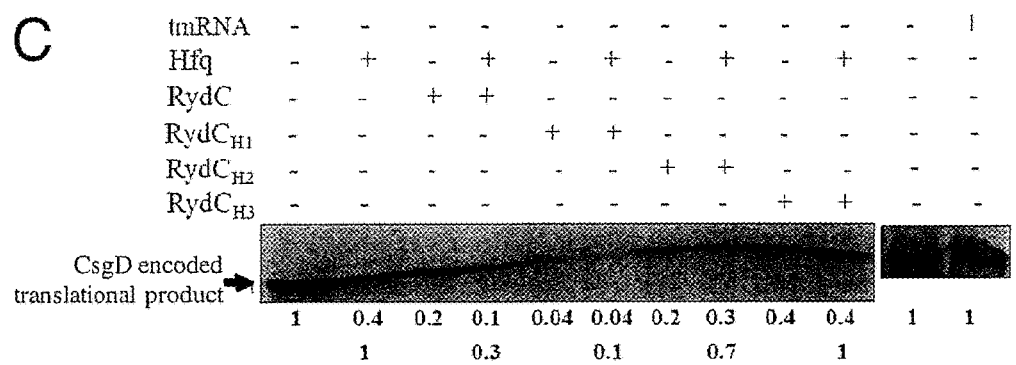
Figure 7 D and C

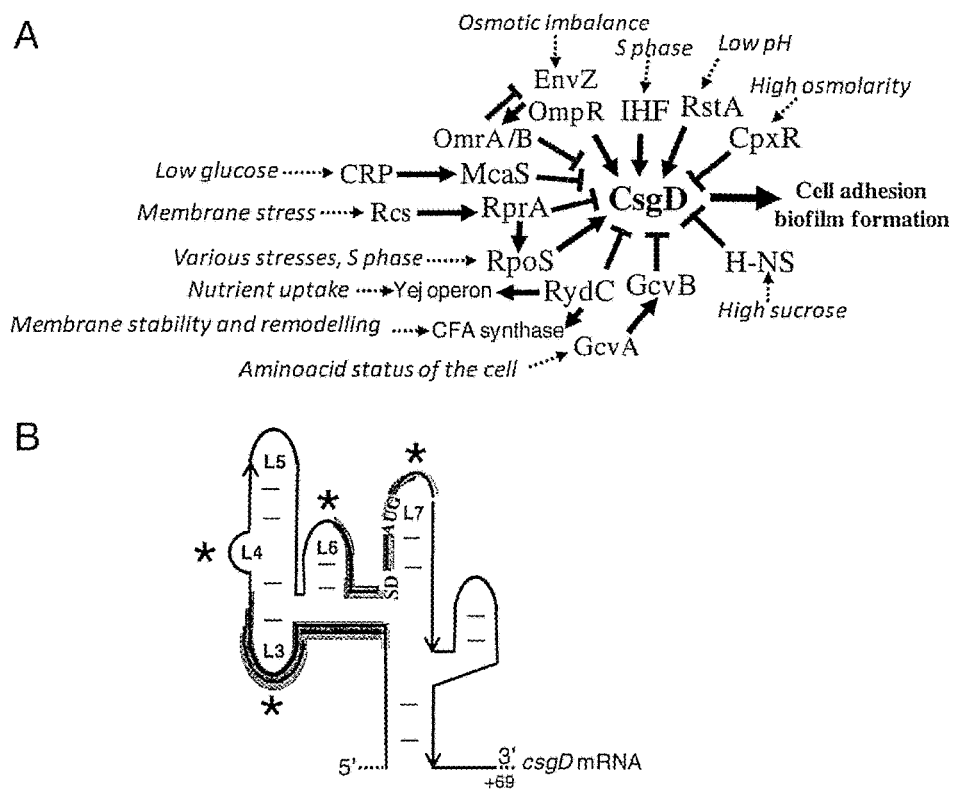
Figure 8 A and B

```
                       SEQUENCE LISTING

<160> NUMBER OF SEQ ID NOS: 15

<210> SEQ ID NO 1
<211> LENGTH: 64
<212> TYPE: RNA
<213> ORGANISM: Salmonella typhimurium

<400> SEQUENCE: 1
uuccgaugua gacccguccu ccuucgccug cgucacgggu ccugguuaga cgcaggcguu    60
uucu                                                                64

<210> SEQ ID NO 2
<211> LENGTH: 64
<212> TYPE: RNA
<213> ORGANISM: Salmonella bongori

<400> SEQUENCE: 2
uuccgaugua gacccgcucu ucuucgccug cgucacgggu cucaauuaga cgcaggcguu    60
uucu                                                                64

<210> SEQ ID NO 3
<211> LENGTH: 62
<212> TYPE: RNA
<213> ORGANISM: Artificial
<220> FEATURE:
<223> OTHER INFORMATION: Synthetic Citrobacter koseri RydC small RNA

<400> SEQUENCE: 3
uuccgaugua gacccguuuc cuucaccugc gucacggguc ugguuacacg cagguguuuu    60
``` cu                                                                          62

<210> SEQ ID NO 4
<211> LENGTH: 63
<212> TYPE: RNA
<213> ORGANISM: Escherichia coli

<400> SEQUENCE: 4
cuuccgaugu agacccguau ucuucgccug uaccacgggu cgguuuuagu acaggcguuu    60
ucu                                                                         63

<210> SEQ ID NO 5
<211> LENGTH: 62
<212> TYPE: RNA
<213> ORGANISM: Shigella flexneri

<400> SEQUENCE: 5
uuccgaugua gacccguauu cuucgccugu accacggguc gguuuuagua caggcguuuu    60
cu                                                                          62

<210> SEQ ID NO 6
<211> LENGTH: 62
<212> TYPE: RNA
<213> ORGANISM: Escherichia fergusonii

<400> SEQUENCE: 6
uuccgaugua gacccguaug cuucgccugc accacggguc ugguuaggug caggcguuuu    60
au                                                                          62

<210> SEQ ID NO 7
<211> LENGTH: 60
<212> TYPE: RNA
<213> ORGANISM: Enterobacter aerogenes

<400> SEQUENCE: 7
uuccgaugua gacccaccuu ucaccugcac uaugggucug guugcgugca ggugucuucu    60

<210> SEQ ID NO 8
<211> LENGTH: 61
<212> TYPE: RNA
<213> ORGANISM: Klebsiella pneumoniae

<400> SEQUENCE: 8
uuccgauguu ggcccgccag uuaaccugca cgccgggccu guuuaggugc agguuuuuc     60 a                                                                           61

<210> SEQ ID NO 9
<211> LENGTH: 215
<212> TYPE: RNA
<213> ORGANISM: Escherichia coli

<400> SEQUENCE: 9
gauguaaucc auuaguuuua uauuuuaccc auuuagggcu gauuuauuac uacacacagc    60
agugcaacau cugucaguac uucugguugcu ucuauuuuag aggcagcugu caggugugcg   120
aucaauaaaa aaagcggggu uucaucaugu uuaaugaagu ccauaguauu cauggucaua   180
cauuauuguu gaucacuaaa ucuucuuugc aggcg                              215

<210> SEQ ID NO 10

```
<211> LENGTH: 18
<212> TYPE: DNA
<213> ORGANISM: Artificial
<220> FEATURE:
<223> OTHER INFORMATION: Synthetic RydC 1-2tot

<400> SEQUENCE: 10
aacatgatga aaccccgc                                                 18

<210> SEQ ID NO 11
<211> LENGTH: 18
<212> TYPE: DNA
<213> ORGANISM: Artificial
<220> FEATURE:
<223> OTHER INFORMATION: Synthetic McaS oligonucleotide

<400> SEQUENCE: 11
tgcactgctg cgtgtgta                                                 18

<210> SEQ ID NO 12
<211> LENGTH: 64
<212> TYPE: RNA
<213> ORGANISM: Escherichia coli

<400> SEQUENCE: 12
cuuccgaugu agacccguau ucuucgccug uaccacgggu cgguuuuagu acaggcguuu   60
ucuu                                                                64

<210> SEQ ID NO 13
<211> LENGTH: 64
<212> TYPE: RNA
<213> ORGANISM: Artificial
<220> FEATURE:
<223> OTHER INFORMATION: Synthetic Escherichia coli RydC H1

<400> SEQUENCE: 13
cuuccgaugu agacccguau ucuucgccug uaccugccca ggguuuuagu acaggcguuu   60
ucuu                                                                64

<210> SEQ ID NO 14
<211> LENGTH: 64
<212> TYPE: RNA
<213> ORGANISM: Artificial
<220> FEATURE:
<223> OTHER INFORMATION: Synthetic Escherichia coli RydC H2

<400> SEQUENCE: 14
cuuccgaugu acugggcaau ucuucgccug uaccacgggu cgguuuuagu acaggcguuu   60
ucuu                                                                64

<210> SEQ ID NO 15
<211> LENGTH: 64
<212> TYPE: RNA
<213> ORGANISM: Artificial
<220> FEATURE:
<223> OTHER INFORMATION: Synthetic Escherichia coli RydC H3

<400> SEQUENCE: 15
cuuccgaugu acugggcaau ucuucgccug uaccugccca ggguuuuagu acaggcguuu   60
ucuu                                                                64
```

OLIGONUCLEOTIDES AND METHODS FOR INHIBITING OR REDUCING BACTERIAL BIOFILMS

CROSS-REFERENCE TO RELATED APPLICATIONS

This application is a national stage patent filing from PCT/IB2015/000212 filed Jan. 29, 2015, which claimed priority to U.S. Ser. No. 61/933,025 filed Jan. 29, 2014.

FIELD OF THE INVENTION

The present invention relates to oligonucleotides useful for inhibiting or reducing bacterial biofilms.

BACKGROUND OF THE INVENTION

Many bacterial small RNAs (sRNAs) modulate gene expression by base-pairing with target mRNAs (1). Trans-encoded sRNAs regulate mRNA expression through small, discontinuous seed-pairings' which are usually at or near the translation initiation signals (TIS) of their targets, whereas cis-antisense sRNAs (asRNAs) are encoded on the DNA strand opposite to that of their targets (2). In the cellular transcript overflow, each of these base-pairing sRNAs has to efficiently locate and bind to its mRNA target, recognizing these through high-affinity contacts made by a few accessible nucleotides. These are usually situated in single-strands (i.e. C-rich stretches), in loops of the regulator, in the target(s), or in both places. After this primary interaction, the structure of the two RNAs is generally rearranged and additional base pairs are formed. In Gram-negative bacteria, the Hfq RNA-binding protein is usually required for transen-coded sRNA stability and operation (2). Hfq facilitates sRNA-mRNA base-pairing by binding both RNAs simultaneously and/or by changing one or both of the RNA structures (3), but its exact contribution at a molecular level remains, for the most part, unresolved.

RydC is a trans-encoded sRNA expressed by enteric bacteria that folds as a pseudoknot and interacts with Hfq, a protein that positively influences sRNA stability in vivo (4). In *Escherichia coli*, RydC controls yejABEF mRNA expression producing an inner membrane ABC transporter (4). yejABEF allows the uptake of translation inhibitor microcin C, a peptide-nucleotide antibiotic targeting aspartyl-tRNA synthetase (5). In *Salmonella*, the yej operon is involved in virulence, interferes with MHC I presentation, counteracts antimicrobial peptides, and provides a nutritious peptide source for survival and proliferation inside the host (6). In intracellular *Salmonella typhimurium*, RydC expression is repressed (7), and perhaps, as is the case for *E. coli*, this is to reduce nutrient uptake by lowering yej mRNA levels (4). In *Salmonella*, RydC selectively activates the longer isoform of the cyclopropane fatty acid synthase mRNA in order to regulate membrane stability (8).

Many bacteria switch between a single-cell motile lifestyle and multi-cellular, sessile adhesive states forming biofilm, resulting in a protected growth mode which allows cells to survive and thrive in hostile environments (9). Biofilm formation is a complex process involving numerous sensory signals linked to elaborate gene regulations via a transcription factor array. When enteric bacteria construct biofilms, they involve curli-specific genes (csg) organised in the csgDEFG and csgBAC bicistronic operon. csgEFG is required for export, and CsgD is a member of the LuxR family of transcriptional regulators that activate csgBA to synthesize the structural components of curli fimbriae. CsgD governs the synthesis of the extracellular matrix components cellulose and curli fimbriae in enteric bacteria responsible for the 'rdar' morphotype (10). A collection of environmental alerts adjust CsgD expression, causing it to swap from a mobile to an attached mode (11). The csgD promoter is positively regulated by several transcription factors (11) and by small signalling molecules (12), whereas its expression is negatively controlled at the posttranscriptional level by five sRNAs acting in collaboration with Hfq. In response to various environmental signals, OmrA/B (13), McaS (14), RprA (15), and GcvB (16) all downregulate CsgD translation by binding at specific locations onto the csgD mRNA 5' untranslated region (UTR), which is a signal perception platform (17).

Accordingly, there is a need to develop new compounds that will be suitable for inhibiting bacterial adhesion and aggregation and biofilms formation, and new drugs that will be suitable for preventing or treating infection from a biofilm. In this way, it has been suggested that characterization of new anti-bacterial compounds for inhibiting bacterial adhesion and aggregation and biofilms formation and for treatment or prevention of infection from a biofilm may be highly desirable.

There is no disclosure in the art of the role of RydC in bacterial adhesion, aggregation and biofilms formation, nor the use of RydC in the prevention or treatment of infection from a biofilm.

SUMMARY OF THE INVENTION

The present invention relates to oligonucleotides useful for inhibiting or reducing bacterial biofilms.

DETAILED DESCRIPTION OF THE INVENTION

In the present invention, the inventors report that RydC reduces expression of curli specific gene D transcription factor required for adhesion and biofilm production in enterobacteria such as *E. coli* and *Salmonella enterica*. RydC pseudoknot aided by Hfq is a dynamic regulatory module. The inventors demonstrated that during curli formation, csgD mRNA synthesis increases when endogenous levels of RydC are lacking. Experimental evidence provided in the present invention shows that RydC, with the help of Hfq, negatively controls csgD mRNA and protein levels. It diminishes csgA and csgBA mRNA and protein levels as well, thus attenuating curli synthesis and biofilm production. CsgD regulation by RydC occurs by direct pairing at the csgD mRNA translation initiation signals (TIS), preventing translation initiation. Upon complex formation with the csgD mRNA, probing and mutational data indicate that RydC induces a structural rearrangement of the csgD mRNA TIS, and the sRNA pseudoknot partially unfolds its 5'-domain to pair with its mRNA target. In the absence of sRNA, Hfq acts as a repressor of csgD mRNA translation, but it promotes complex formation between the two RNAs, presumably by facilitating pseudoknot opening to increase accessibility to the RydC 5'-domain. This makes RydC the sixth sRNA to negatively influence the expression of the csgD transcription factor that regulates collective behaviour in enteric bacteria, determining progression from a planktonic to a sessile condition.

Oligonucleotides of the Invention

One aspect of the invention relates to an oligonucleoltide that recognizes and targets (e.g. hybridizes) the CsgD mRNA (such as SEQ ID NO:9), even more particularly the CsgD translation initiation signals (TIS) and thus impends the synthesis of CsgD.

In some embodiments, the oligonucleotide of the present invention hybridizes to the CsgD mRNA sequence ranging from nucleic acid at position 128 to nucleic acid at position 151 in SEQ ID NO: 9 and thus blocks the translation of said CsgD mRNA.

In some embodiments, the oligonucleotide of the present invention hybridizes to the CsgD mRNA sequence ranging from nucleic acid at position 128 to nucleic acid at position 149 in SEQ ID NO: 9 and thus blocks the translation of said CsgD mRNA.

In some embodiments, the oligonucleotide of the present invention hybridizes to the CsgD mRNA sequence ranging from nucleic acid at position 134 to nucleic acid at position 151 in SEQ ID NO: 9 and thus blocks the translation of said CsgD mRNA.

The term "RydC" has its general meaning in the art and refers to a Small regulatory RNAs (sRNA) expressed in enteric bacteria. The term "RydC" refers to trans-encoded sRNA expressed by enteric bacteria that folds as a pseudoknot and interacts with Hfq, a protein that positively influences sRNA stability in vivo (4). The term "RydC" also refers to a sRNA that controls yejABEF mRNA expression producing an inner membrane ABC transporter (4).

The term "CsgD" has its general meaning in the art and refers to curli-specific genes (csg). The term "CsgD" relates to curli-specific genes (csg) involved in enteric bacteria construct biofilms, CsgD is organised in the csgDEFG and csgBAC bicistronic operon. CsgD is a member of the LuxR family of transcriptional regulators that activate csgBA to synthesize the structural components of curli fimbriae. CsgD governs the synthesis of the extracellular matrix components cellulose and curli fimbriae in enteric bacteria responsible for the 'rdar' morphotype (10). A collection of environmental alerts adjust CsgD expression, causing it to swap from a mobile to an attached mode (11). The csgD promoter is positively regulated by several transcription factors (11) and by small signalling molecules (12), whereas its expression is negatively controlled at the post-transcriptional level by five sRNAs acting in collaboration with Hfq. In response to various environmental signals, OmrA/B (13), McaS (14), RprA (15), and GcvB (16) all downregulate CsgD translation by binding at specific locations onto the csgD mRNA 5' untranslated region (UTR), which is a signal perception platform (17).

The term "nucleotide" as used herein is defined as a modified or naturally occurring deoxyribonucleotide or ribonucleotide. Nucleotides typically include purines and pyrimidines, which include thymidine, cytidine, guanosine, adenine and uridine. The term "oligonucleotide" as used herein is defined as an oligomer of the nucleotides defined above. The term also includes "oligonucleotide analog" which refers to an oligonucleotide having (i) a modified backbone structure, e.g., a backbone other than the standard phosphodiester linkage found in natural oligo- and polynucleotides, and (ii) optionally, modified sugar moieties, e.g., morpholino moieties rather than ribose or deoxyribose moieties. Oligonucleotide analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone. A substantially uncharged, phosphorus containing backbone in an oligonucleotide analog is one in which a majority of the subunit linkages, e.g., between 50-100%, typically at least 60% to 100% or 75% or 80% of its linkages, are uncharged, and contain a single phosphorous atom.

The oligonucleotide of the invention may be of any suitable type.

In some embodiments, the oligonucleotide is a RNA oligonucleotide.

In some embodiments, the oligonucleotide is a DNA oligonucleotide.

The one skilled in the art can easily provide some modifications that will improve the efficacy of the oligonucleotide (C. Frank Bennett and Eric E. Swayze, RNA Targeting Therapeutics: Molecular Mechanisms of Antisense Oligonucleotides as a Therapeutic Platform Annu. Rev. Pharmacol. Toxicol. 2010.50:259-293.). Typically, chemical modifications include backbone modifications, heterocycle modifications, sugar modifications, and conjugations strategies. For example the oligonucleotide may be selected from the group consisting of oligodeoxyribonucleotides, oligoribonucleotides, LNA, oligonucleotide, morpholinos, small regulatory RNAs (sRNAs), tricyclo-DNA-antisense oligonucleotides (ASOs), U7- or U1-mediated ASOs or conjugate products thereof such as peptide-conjugated or nanoparticle-complexed ASOs. Indeed, for use in vivo, the oligonucleotide may be stabilized. A "stabilized" oligonucleotide refers to an oligonucleotide that is relatively resistant to in vivo degradation (e.g. via an exo- or endo-nuclease). Stabilization can be a function of length or secondary structure. In particular, oligonucleotide stabilization can be accomplished via phosphate backbone modifications.

In a particular embodiment, the oligonucleotide according to the invention is a LNA oligonucleotide. As used herein, the term "LNA" (Locked Nucleic Acid) (or "LNA oligonucleotide") refers to an oligonucleotide containing one or more bicyclic, tricyclic or polycyclic nucleoside analogues also referred to as LNA nucleotides and LNA analogue nucleotides. LNA oligonucleotides, LNA nucleotides and LNA analogue nucleotides are generally described in International Publication No. WO 99/14226 and subsequent applications; International Publication Nos. WO 00/56746, WO 00/56748, WO 00/66604, WO 01/25248, WO 02/28875, WO 02/094250, WO 03/006475; U.S. Pat. Nos. 6,043,060, 6,268,490, 6,770,748, 6,639,051, and U.S. Publication Nos. 2002/0125241, 2003/0105309, 2003/0125241, 2002/0147332, 2004/0244840 and 2005/0203042, all of which are incorporated herein by reference. LNA oligonucleotides and LNA analogue oligonucleotides are commercially available from, for example, Proligo LLC, 6200 Lookout Road, Boulder, Colo. 80301 USA.

Other possible stabilizing modifications include phosphodiester modifications, combinations of phosphodiester and phosphorothioate modifications, methylphosphonate, methylphosphorothioate, phosphorodithioate, p-ethoxy, and combinations thereof. Chemically stabilized, modified versions of the oligonucleotide also include "Morpholinos" (phosphorodiamidate morpholino oligomers, PMOs), 2'-O-Met oligomers, tricyclo (tc)-DNAs, U7 short nuclear (sn) RNAs, or tricyclo-DNA-oligoantisense molecules (U.S. Provisional Patent Application Ser. No. 61/212,384 For: Tricyclo-DNA Antisense Oligonucleotides, Compositions and Methods for the Treatment of Disease, filed Apr. 10, 2009, the complete contents of which is hereby incorporated by reference).

Other forms of oligonucleotides of the present invention are oligonucleotide sequences coupled to small nuclear RNA molecules such as U1 or U7 in combination with a viral transfer method based on, but not limited to, lentivirus or adeno-associated virus (Denti, M A, et al, 2008; Goyenvalle, A, et al, 2004).

Other forms of oligonucleotides of the present invention are peptide nucleic acids (PNA). In peptide nucleic acids, the deoxyribose backbone of oligonucleotides are replaced with a backbone more akin to a peptide than a sugar. Each subunit, or monomer, has a naturally occurring or non naturally occurring base attached to this backbone. One such backbone is constructed of repeating units of N-(2-aminoethyl)glycine linked through amide bonds. Because of the radical deviation from the deoxyribose backbone, these compounds were named peptide nucleic acids (PNAs) (Dueholm et al., New J. Chem., 1997, 21, 19-31).

PNA binds both DNA and RNA to form PNA/DNA or PNA/RNA duplexes. The resulting PNA/DNA or PNA/RNA duplexes are bound with greater affinity than corresponding DNA/DNA, DNA/RNA or RNA/RNA duplexes as determined by Tm's. This high thermal stability might be attributed to the lack of charge repulsion due to the neutral backbone in PNA. The neutral backbone of the PNA also results in the Tm's of PNA/DNA(RNA) duplex being practically independent of the salt concentration. Thus the PNA/DNA(RNA) duplex interaction offers a further advantage over DNA/DNA, DNA/RNA or RNA/RNA duplex interactions which are highly dependent on ionic strength. Homopyrimidine PNAs have been shown to bind complementary DNA or RNA in an anti-parallel orientation forming (PNA)2/DNA(RNA) triplexes of high thermal stability (see, e.g., Egholm, et al., Science, 1991, 254, 1497; Egholm, et al., J. Am. Chem. Soc., 1992, 114, 1895; Egholm, et al., J. Am. Chem. Soc., 1992, 114, 9677).

In addition to increased affinity, PNA has also been shown to bind to DNA or RNA with increased specificity. When a PNA/DNA duplex mismatch is melted relative to the DNA/DNA duplex there is seen an 8 to 20° C. drop in the Tm. This magnitude of a drop in Tm is not seen with the corresponding DNA/DNA duplex with a mismatch present.

The binding of a PNA strand to a DNA or RNA strand can occur in one of two orientations. The orientation is said to be anti-parallel when the DNA or RNA strand in a 5' to 3' orientation binds to the complementary PNA strand such that the carboxyl end of the PNA is directed towards the 5' end of the DNA or RNA and amino end of the PNA is directed towards the 3' end of the DNA or RNA. In the parallel orientation the carboxyl end and amino end of the PNA are just the reverse with respect to the 5'-3' direction of the DNA or RNA.

A further advantage of PNA compared to oligonucleotides is that their polyamide backbones (having appropriate nucleobases or other side chain groups attached thereto) is not recognized by either nucleases or proteases and are not cleaved. As a result PNAs are resistant to degradation by enzymes unlike nucleic acids and peptides.

PCT/EP/01219 describes novel peptide nucleic acid (PNA) compounds which bind complementary DNA and RNA more tightly than the corresponding DNA. PNA have shown strong binding affinity and specificity to complementary DNA (Egholm, M., et al., Chem. Soc., Chem. Commun., 1993, 800; Egholm, M., et. al., Nature, 1993, 365, 566; and Nielsen, P., et. al. Nucl. Acids Res., 1993, 21, 197). Furthermore, PNA's show nuclease resistance and stability in cell-extracts (Demidov, V. V., et al., Biochem. Pharmacol., 1994, 48, 1309-1313). Modifications of PNA include extended backbones (Hyrup, B., et. al. Chem. Soc., Chem. Commun., 1993, 518), extended linkers between the backbone and the nucleobase, reversal of the amida bond (Lagriffoul, P. H., et. al., Biomed. Chem. Lett., 1994, 4, 1081), and the use of a chiral backbone based on alanine (Dueholm, K. L., et. al., BioMed. Chem. Lett., 1994, 4, 1077).

Peptide Nucleic Acids are described in U.S. Pat. Nos. 5,539,082 and 5,539,083. Peptide Nucleic Acids are further described in U.S. patent application Ser. No. 08/686,113.

In some embodiments, the oligonucleotide of the invention comprises or consists of i) a nucleic acid sequence ranging from nucleic acid at position 1 to nucleic acid at position 24 in SEQ ID NO: 1, nucleic acid at position 1 to nucleic acid at position 24 in SEQ ID NO: 2, nucleic acid at position 1 to nucleic acid at position 23 in SEQ ID NO: 3, nucleic acid at position 1 to nucleic acid at position 24 in SEQ ID NO: 4, nucleic acid at position 1 to nucleic acid at position 23 in SEQ ID NO: 5, nucleic acid at position 1 to nucleic acid at position 23 in SEQ ID NO: 6, nucleic acid at position 1 to nucleic acid at position 21 in SEQ ID NO: 7, nucleic acid at position 1 to nucleic acid at position 22 in SEQ ID NO: 8, nucleic acid sequence SEQ ID NO: 10, or ii) a nucleic acid sequence having at least 70% of identity with the nucleic acid sequence ranging from nucleic acid at position 1 to nucleic acid at position 24 in SEQ ID NO: 1, nucleic acid at position 1 to nucleic acid at position 24 in SEQ ID NO: 2, nucleic acid at position 1 to nucleic acid at position 23 in SEQ ID NO: 3, nucleic acid at position 1 to nucleic acid at position 24 in SEQ ID NO: 4, nucleic acid at position 1 to nucleic acid at position 23 in SEQ ID NO: 5, nucleic acid at position 1 to nucleic acid at position 23 in SEQ ID NO: 6, nucleic acid at position 1 to nucleic acid at position 21 in SEQ ID NO: 7, nucleic acid at position 1 to nucleic acid at position 22 in SEQ ID NO: 8, nucleic acid sequence SEQ ID NO: 10.

In some embodiments the oligonucleotide does not consist of the nucleic acid sequence of *Salmonella bongori* RydC, *Citrobacter koseri* RydC, *Escherichia coli* RydC, *Shigella flexneri* RydC, *Escherichia fergusoni* RydC, *Enterobacter aerogenes* RydC, *Klebsiella pneumonia* RydC.

According to the invention a first nucleic acid sequence having at least 70% of identity with a second nucleic acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99% of identity with the second nucleic acid sequence. Nucleic acid sequence identity is preferably determined using a suitable sequence alignment algorithm and default parameters, such as BLAST N (Karlin and Altschul, Proc. Natl Acad. Sci. USA 87(6): 2264-2268 (1990)).

Typically the oligonucleotides of the present invention are obtained by conventional methods well known to those skilled in the art. For example, the oligonucleotide of the invention can be synthesized de novo using any of a number of procedures well known in the art. For example, the b-cyanoethyl phosphoramidite method (Beaucage et al., 1981); nucleoside H-phosphonate method (Garegg et al., 1986; Froehler et al., 1986, Garegg et al., 1986, Gaffney et al., 1988). These chemistries can be performed by a variety of automated nucleic acid synthesizers available in the market. These nucleic acids may be referred to as synthetic nucleic acids. Alternatively, oligonucleotide can be produced on a large scale in plasmids (see Sambrook, et al., 1989). Oligonucleotide can be prepared from existing nucleic acid sequences using known techniques, such as those employing restriction enzymes, exonucleases or endonucleases. Oligonucleotide prepared in this manner may be referred to as isolated nucleic acids.

In a particular embodiment, the oligonucleotide of the present invention is conjugated to a second molecule. Typically said second molecule is selected from the group consisting of aptamers, antibodies or polypeptides. For example, the oligonucleotide of the present invention may be conjugated to a cell or bacterial penetrating peptide. Cell penetrating peptides are well known in the art and include for example the TAT peptide (Bechara C, Sagan S. Cell-penetrating peptides: 20 years later, where do we stand? FEBS Lett. 2013 Jun. 19; 587(12):1693-702; Malhi S S, Murthy R S. Delivery to mitochondria: a narrower approach for broader therapeutics. Expert Opin Drug Deliv. 2012 August; 9(8):909-35; Wesolowski D, Alonso D, Altman S. Combined effect of a peptide-morpholino oligonucleotide conjugate and a cell-penetrating peptide as an antibiotic. Proc Natl Acad Sci USA. 2013 May 21; 110(21):8686-9). The oligonucleotide of the present invention may be conjugated to cell penetrating peptide described in Wesolowski D, Tae H S, Gandotra N, Llopis P, Shen N, Altman S. Basic peptide-morpholino oligomer conjugate that is very effective in killing bacteria by gene-specific and nonspecific modes. Proc Natl Acad Sci USA. 2011 Oct. 4; 108(40): 16582-7. In a particular embodiment, the oligonucleotide-second molecule conjugate is able to target the enteric bacteria infected cells. In a particular embodiment, the oligonucleotide-second molecule conjugate targets CsgD. In a particular embodiment, the oligonucleotide-second molecule conjugate is able to target the bacteria *Escherichia coli* and *Salmonella typhimurium* strain.

Methods and Uses of the Invention

A further aspect of the invention relates to a method of inhibiting or reducing bacterial biofilm formation on a surface comprising the step of applying to the surface of an amount of an oligonucleotide according to the invention.

The term "bacterial biofilm" has its general meaning in the art and refers to structured communities or aggregates of bacterial cells in which cells adhere to each other and/or to a living or inert (non-living) surface. These adherent cells are frequently embedded within a self-produced matrix of extracellular polymeric substance. Biofilms represent a prevalent mode of microbial life in natural, industrial and hospital settings. Biofilms can contain many different types of microorganism, e.g. bacteria, archaea, protozoa, fungi and algae.

In some embodiments, the biofilm is produced by enteric bacteria. The term "enteric bacteria" has its general meaning in the art and refers to bacteria that occur normally or pathogenically in intestines of humans and other animals. The term "enteric bacteria" refers to but it is not limited to gram-negative bacteria *Escherichia coli*, and *Salmonella*, e.g. *S. Typhimurium, S. Enteritidis, S. arizonae, S. bongori, S. cholerae-suis, S. choleraesuis, S. enterica, S. paratyphi, S. pullorum, S. subterranea*, and *S. typhi*, and *Klebsiella pneumoniae, Pseudomonas*, e.g; a bacterium of the *Pseudomonas aeruginosa* group such as *P. aeruginosa* group *P. aeruginosa, P. alcaligenes, P. anguilliseptica, P. argentinensis, P. borbori, P. citronellolis, P. flavescens, P. mendocina, P. nitroreducens, P. oleovorans, P. pseudoalcaligenes, P. resinovorans, P. straminea, Citrobacter koseri, Shigella flexneri, Escherichia fergusoni, Enterobacter aerogenes*, or *Klebsiella pneumonia*.

As used herein the term "surface" refers to any surface where bacteria (e.g. enteric bacteria) are liable to grow on.

In some embodiments, the surface is an artificial surface or is a biological surface.

Typically, artificial surfaces include but are not limited to surfaces that can be used for medical, sanitary, veterinary, food preparation (e.g. food industry), agribusiness or agronomic purposes. Typically, the material is made of plastic, metal, glass or polymers. In some embodiments, the surface is any surface that constitutes an environment wherein development of enteric bacteria is not desirable (e.g. hospitals, intensive care units, dental offices . . . ). For example, the surface is a surface of hospital furniture, non implantable and implantable devices or medical tools that are liable to be in contact with patients.

In some embodiments, the oligonucleotide of the present invention is applied to a surface of a material.

As used herein, the term "material" denotes any material for any purposes, including but not limiting to, research purposes, diagnostic purposes, and therapeutic purposes. Typically the material is a natural material or is an artificial material (i.e. a man-made material). The material can be less or more solid, less or more flexible, can have less or ability to swell . . . . In some embodiments, the material is an artificial material. Typically the material is selected form the group consisting of membranes, scaffold materials, films, sheets, tapes, patches, meshes or medical devices.

In some embodiments, the material is biocompatible material. As used herein, the term "biocompatible" generally refers having the property or characteristic of not generating injury, toxicity or immunological reaction to living tissues. Accordingly, the material does not substantively provoke injury, toxicity or an immunological reaction, such as a foreign body reaction or inflammatory response (in particular excessive inflammatory response), upon for example implantation of the material in a subject.

In some embodiments, the material is biodegradable. The term "biodegradable" as used herein is defined to include both bioabsorbable and bioresorbable materials. In particular, by "biodegradable", it is meant that the materials decompose, or lose structural integrity under body conditions (e.g., enzymatic degradation or hydrolysis) or are broken down (physically or chemically) under physiologic conditions in the body such that the degradation products are excretable or absorbable by the body.

Typically the material may be made from any biocompatible polymer. The biocompatible polymer may be synthetic or natural. The biocompatible polymer may be biodegradable, non-biodegradable or a combination of biodegradable and non-biodegradable.

Representative natural biodegradable polymers which may be used include but are not limited to polysaccharides, such as alginate, dextran, chitin, hyaluronic acid, cellulose, collagen, gelatin, fucans, glycosaminoglycans, and chemical derivatives thereof (substitutions and/or additions of chemical groups, for example, alkyl, alkylene, hydroxylations, oxidations, and other modifications routinely made by those skilled in the art); and proteins, such as albumin, casein, zein, silk, and copolymers and blends thereof, alone or in combination with synthetic polymers.

Synthetically modified natural polymers which may be used include but are not limited to cellulose derivatives, such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These are collectively referred to herein as "celluloses."

Representative synthetic degradable polymers suitable for use include but are not limited to polyhydroxy acids prepared from lactone monomers, such as glycolide, lactide, caprolactone, ϵ-caprolactone, valerolactone, and δ-valerolactone, as well as pluronics, carbonates (e.g., trimethylene carbonate, tetramethylene carbonate, and the like); dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactide-co-(s-caprolactone-)); poly(glycolide-co-(8-caprolactone)); polycarbonates; poly(pseudo amino acids); poly(amino acids); poly(hydroxyalkanoate)s; polyalkylene oxalates; polyoxaesters; polyanhydrides; polyortho esters; and copolymers, block copolymers, homopolymers, blends, and combinations thereof.

Some non-limiting examples of suitable non-bioabsorbable materials include but are not limited to polyolefins, such as polyethylene and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins, such as fluoroethylenes, fluoropropylenes, fluoroPEGSs, and polytetrafluoroethylene; polyamides, such as nylon and polycaprolactam; polyamines; polyimines; polyesters, such as polyethylene terephthalate and polybutylene terephthalate; aliphatic polyesters; polyethers; polyether-esters, such as polybutester; polytetramethylene ether glycol; 1,4-butanediol; polyurethanes; acrylic polymers and copolymers; modacrylics; vinyl halide polymers and copolymers, such as polyvinyl chloride; polyvinyl alcohols; polyvinyl ethers, such as polyvinyl methyl ether; polyvinylidene halides, such as polyvmylidene fluoride and polyvinylidene chloride; polyacrylonitrile; polyaryletherketones; polyvinyl ketones; polyvinyl aromatics, such as polystyrene; polyvinyl esters, such as polyvinyl acetate; copolymers of vinyl monomers with each other and olefins, such as etheylene-methyl methacrylate copolymers, acrylonitrile-styrene copolymers, ABS resins, and ethylene-vinyl acetate copolymers; alkyd resins; polycarbonates; polyoxymethylenes; polyphosphazine; polyimides; epoxy resins; aramids, rayon; rayon-triacetate; spandex; silicones; and combinations thereof.

In some embodiments, the material comprises a wowen or non wowen fabric used as biomedical prostheses and scaffolds for tissue engineering. They can be biodegradable or not in nature and are obtained by numerous manufactured methods including electrospinning to have small pore size, high porosity and high surface area.

In some embodiment, the material is a mesh, in particular a surgical mesh. As used herein, the term "mesh" is intended to include any element having an openwork fabric or structure, and may include but is not limited to, an interconnected network of wire-like segments, a sheet of material having numerous apertures and/or portions of material removed, or the like. As used herein the term "surgical mesh" is used to a mesh suitable for use in surgical procedures, such as, for example, meshes that do not require suturing to the abdominal wall. Surgical meshes, which are used to reinforce weakened areas of abdominal, pelvic, or thoracic tissues, or to replace a portion of internal structural soft tissue that has neither been damaged nor removed surgically, can also be made to have anti-adhesion properties. Surgical mesh drug eluting delivery devices can include one or more therapeutic agents provided with a drug eluting mesh wrap implant placed adjacent to medical devices and internal tissue as described therein. The meshes are available in various single layer, multi-layer, and 3-dimensional configurations made without bioabsorbable adhesion coatings and films. The meshes are most often constructed of synthetic non-absorbable polymer materials, such as polyethylene, polytetrafluoroethylene, and polypropylene, and can include a carrier having a therapeutic agent attached thereto, incorporated within, or coated thereon. Typically four different material groups have become available for hernia repair and abdominal wall reconstruction: PP, PTFE, ePTFE and Polyester (POL) (Yilmaz Bilsel, Ilker Abci The search for ideal hernia repair; mesh materials and types International Journal of Surgery 10 (2012) 317e321). PP is a hydrophobic polymer of carbon atoms with alternating methyl moieties. This material is flexible, strong, easily cut, readily integrated by surrounding tissues and resists infection. The monofilament nature provides large pores facilitating fibrovascular ingrowth, infection resistance and improved compliance. PP remains the most popular material in mesh hernia repair. PTFE is a chemically inert synthetic fluoropolymer which has a high negative charge, therefore water and oils do not adhere to it. This material does not incorporate into human tissue and becomes encapsulated. Poor tissue incorporation increases hernia recurrence and an infected PTFE mesh must be explanted. PTFE is micro porous, which allows bacteria passage but prevents macrophage passage; therefore the body cannot clear the infection. 8 and 9 PTFE was expanded to be improved, and it became a uniform, fibrous and micro porous structure with improved strength called ePTFE. Although it is not incorporated into tissue and has a high incidence of seroma formation, ePTFE remains inert and produces little inflammatory effects, which allows it to be placed directly on viscera. POL is a carbon polymer of terepthalic acid and can be fashioned into strong fibers suitable to be woven into a prosthetic mesh. It is a hydrophilic material and is degraded by hydrolysis. The mesh structure for this surgical application serves as a drug eluting delivery apparatus for local therapeutic delivery within the body. Affixing the carrier and or coating directly onto the surgical mesh makes it easier to handle the device without the drawbacks of film, namely tearing, folding, and rapid dissolving when contacting body fluids, and the lack of fixation or anchoring means. Non-absorbable mesh structures generally provide more handling strength and directional placement control during installation than bio-absorbable or bio-dissolvable polymer films.

In some embodiments, the material is an implant. Regular improvements have been made to facilitate the use of implants. These include: preformed or precut implants adapted to different techniques (4D Dome®; Ultrapro Plug®, Perfix Plug®) for the plug techniques; different pre-cut prostheses to allow the passage of the spermatic cord (Lichtenstein technique); meshes that assume the anatomical contours of the inguinal region for the pre-peritoneal technique (ex Swing Mesh 4A®, 3D Max®). In particular, the implant is designed to facilitate its implantation. Implants furnished with either an auto-adhesive cover (example: Swing Contact®, Adhesix®, Progrip®) or with thermo-inducted staples (example: Endorollfix®); Three-dimensional implants theoretically limiting the possibility of migration (example: UHS®, Ultrapro®, 3D Patch®, PHS®); Implants adapted to laparoscopic maneuvering, for example, pre-rolled to facilitate the passage in the trocar (example: Endoroll®), or with pre-inserted cardinal point sutures (example: Parietex®) may be suitable.

In some embodiments, the material is a bioprosthesis. The bioprostheses used in abdominal wall surgery derive from animal (xenogenic prostheses from porcine (dermis or intestinal mucosa) or bovine (pericardium) origin, reticulated or not) or human (allogenic) tissues. They are constituted by type I, III or IV collagen matrixes as well as sterile acellular elastin produced by decellularization, sterilization and viral inactivation, in order to enhance integration and cellular colonization of the prosthesis by the host tissues. Comercial examples include but are not limited to Tutopatch®, SIS®, Tissue Science® process, Surgiguard®, Strattice®, Colla-Mend®, Permacol®, Surgisis®, XenMatrix®, Veritas® (non-reticulated bovine pericardial bioprosthesis), Protexa (porcine dermis), Alloderm®, Flex HD® Acellular Hydrated Dermis and AlloMax™ (formerly Neoform™) (acellular collagen matrix derived from human dermis.

In some embodiments, the material is an orthopaedic implant. Typically, orthopaedic implant include but are not limited to prosthetic knees, hips, shoulders, fingers, elbows, wrists, ankles, fingers and spinal elements.

In some embodiments, the material is a medical device. The medical device can be implanted at a variety of locations in the body including many different subcutaneous and sub-muscular locations.

In some embodiments, the medical devices include those used to sense and/or affect bodily function upon implantation and/or for carrying out various other functions in the body. These can be but are not limited to pacing devices, defibrillators, implantable access systems, monitors, stimulators including neurostimulators, ventricular assist devices, pain pumps, infusion pumps and other implantable objects or systems or components thereof, for example, those used to deliver energy and/or substances to the body and/or to help monitor bodily function. Representative examples include cardiovascular devices (e.g., implantable venous catheters, venous ports, tunneled venous catheters, chronic infusion lines or ports, including hepatic artery infusion catheters, pacemakers and pacemaker leads; neurologic/neurosurgical devices (e.g., ventricular peritoneal shunts, ventricular atrial shunts, nerve stimulator devices, dural patches and implants to prevent epidural fibrosis post-laminectomy, devices for continuous subarachnoid infusions); gastrointestinal devices (e.g., chronic indwelling catheters, feeding tubes, portosystemic shunts, shunts for ascites, peritoneal implants for drug delivery, peritoneal dialysis catheters, and suspensions or solid implants to prevent surgical adhesion); genitourinary devices (e.g., uterine implants, including intrauterine devices (IUDs) and devices to prevent endometrial hyperplasia, fallopian tubal implants, including reversible sterilization devices, fallopian tubal stents, artificial sphincters and periurethral implants for incontinence, ureteric stents, chronic indwelling catheters, bladder augmentations, or wraps or splints for vaso-vasostomy, central venous catheters; prosthetic heart valves, ophthalmologic implants (e.g., multino implants and other implants for neovascular glaucoma, drug eluting contact lenses for pterygiums, splints for failed dacrocystalrhinostomy, drug eluting contact lenses for corneal neovascularity, implants for diabetic retinopathy, drug eluting contact lenses for high risk corneal transplants); cochlear implants; otolaryngology devices (e.g., ossicular implants, Eustachian tube splints or stents for glue ear or chronic otitis as an alternative to transtempanic drains); dental implants, plastic surgery implants (e.g., breast implants or chin implants), catheter cuffs and orthopedic implants (e.g., cemented orthopedic prostheses). Implantable sensors for monitoring conditions such as blood pH, ion concentration, metabolite levels, clinical chemistry analyses, oxygen concentration, carbon dioxide concentration, pressure, and glucose levels are also included. Blood glucose levels, for example, may be monitored using optical sensors and electrochemical sensors.

For example, a pacemaker can be used to maintain a suitable heart rate and rhythm. Typically pacemakers are used to treat fainting spells (syncope), congestive heart failure, hypertrophic cardiomyopathy and other conditions. Different types of pacemakers include but are not limited to single chamber pacemakers; dual chamber pacemakers; and biventricular pacemakers.

A large variety of devices capable of providing stimulation to one or more parts of the body can be used in accordance with the present invention, and in the regard, the targeted implant location for these devices will vary depending on the application. Neurostimulation, muscular stimulation, gastric stimulation and/or other stimulation can be administered via electrodes on the leads and located within or proximate to the target tissue, organ or other body part or system. As examples, implantable medical leads may be positioned proximate to the vagal nerve for delivery of neurostimulation to the vagal nerve. Implantable neurostimulators can be used to send a stimulus, e.g., an electrical signal, via leads to the spine or brain to treat pain and other neurological disorders. Gastrointestinal conditions, severe chronic nausea and vomiting as well as urological disorders can also be treated with appropriate devices as will be understood by those skilled in the art. Chronic pain including back, neck and spinal pain can be treated as well using known devices. Epilepsy and essential tremor including tremors associated with Parkinson's disease and other neurological disorders can be treated in accordance with the present invention. If drug or other delivery systems are used, they will typically include a pump and a catheter for dispensing the substances.

Typically, biological surfaces include but are not limited to plant or animal surface. In some embodiments, the surface is a tissue surface. In some embodiments, the oligonucleotide of the present invention is applied to at least one tissue surface selected from the group consisting of skin tissue, hair tissue, nail tissue, corneal tissue, tongue tissue, oral cavity tissue, esophageal tissue, anal tissue, urethral tissue, vaginal tissue, urinary epithelial tissue, salivary gland tissue, mammary gland tissue, lacrimal gland tissue, sweat gland tissue, prostate gland tissue, bulbourethral gland tissue, Bartholin's gland tissue, uterine tissue, respiratory and gastrointestinal tract goblet cell tissue, gastric mucosal tissue, gastric gland tissue, pancreatic tissue, spleen tissue, pulmonary tissue, pituitary gland tissue, thyroid gland tissue, parathyroid gland tissue, testicular tissue, ovarian tissue, respiratory gland tissue, gastrointestinal gland tissue, adrenal gland tissue, renal tissue, liver tissue, adipose tissue, duct cell tissue, gall bladder tissue, epidydimal tissue, vas deferens tissue, blood vessel tissue, lymph gland tissue, lymphatic duct tissue, synovial tissue, serosal tissue, squamous tissue, cochlear tissue, choroid plexus tissue, ependymal tissue, dural tissue, pia-arachnoid tissue, sclera tissue, retinal tissue, iris tissue, ciliary tissue, dental tissue, otic tissue, ligament tissue, tendon tissue, elastic cartilage tissue, fibrocartilage tissue, hyaline cartilage tissue, bone marrow tissue, intervertebral disc tissue, compact bone tissue, cancellous bone tissue, skeletal muscle tissue, cardiac muscle tissue, smooth muscle tissue, cardiac valve tissue, pericardial tissue, pleural tissue, peritoneal tissue, blood cell tissue, neuronal tissue, glial tissue, sensory transducer cell tissue, pain sensitive tissue, autonomic neuron tissue, peripheral nervous system tissue, cranial nerve tissue, ocular lens tissue, germ cell tissue, thymus tissue, placental tissue, fetal membrane tissue, umbilical tissue, stem cell tissue, mesodermal tissue, ectodermal tissue, endodermal tissue, autologous tissue, allograft tissue or a combination thereof.

In a particular embodiment, the present invention relates to a method of inhibiting or reducing bacterial biofilm formation on a surface comprising the step of applying to the surface an oligonucleotide comprising or consisting of i) a nucleic acid sequence ranging from nucleic acid at position 1 to nucleic acid at position 24 in SEQ ID NO: 1, nucleic acid at position 1 to nucleic acid at position 24 in SEQ ID NO: 2, nucleic acid at position 1 to nucleic acid at position 23 in SEQ ID NO: 3, nucleic acid at position 1 to nucleic acid at position 24 in SEQ ID NO: 4, nucleic acid at position 1 to nucleic acid at position 23 in SEQ ID NO: 5, nucleic acid at position 1 to nucleic acid at position 23 in SEQ ID NO: 6, nucleic acid at position 1 to nucleic acid at position 21 in SEQ ID NO: 7, nucleic acid at position 1 to nucleic acid at position 22 in SEQ ID NO: 8, nucleic acid sequence SEQ ID NO: 10, or ii) a nucleic acid sequence having at least 70% of identity with the nucleic acid sequence ranging from nucleic acid at position 1 to nucleic acid at position 24 in SEQ ID NO: 1, nucleic acid at position 1 to nucleic acid at position 24 in SEQ ID NO: 2, nucleic acid at position 1 to nucleic acid at position 23 in SEQ ID NO: 3, nucleic acid at position 1 to nucleic acid at position 24 in SEQ ID NO: 4, nucleic acid at position 1 to nucleic acid at position 23 in SEQ ID NO: 5, nucleic acid at position 1 to nucleic acid at position 23 in SEQ ID NO: 6, nucleic acid at position 1 to nucleic acid at position 21 in SEQ ID NO: 7, nucleic acid at position 1 to nucleic acid at position 22 in SEQ ID NO: 8, nucleic acid sequence SEQ ID NO: 10.

In some embodiments, the method of the present invention further comprises the step of applying to the surface of at least one compound selected from the group consisting of Hfq polypeptide, curli inhibitor compound, CsgD inhibitor compound, CsgA inhibitor compound, and CsgB inhibitor compound.

The term "Hfq polypeptide" refers to Hfq RNA-binding protein expressed in Gram-negative bacteria. The term "Hfq" also refers to RNA-binding protein usually required for trans-encoded sRNA stability and operation (2), Hfq facilitates sRNA-mRNA base-pairing by binding both RNAs simultaneously and/or by changing one or both of the RNA structures (3).

The term "curli inhibitor compound", "CsgD inhibitor compound", "CsgA inhibitor compound", and "CsgB inhibitor compound" has its general meaning in the art and refers to curli, CsgD, CsgA or CsgB inhibitor of expression or curli, or CsgD, CsgA or CsgB antagonists. As used herein, the term "curli, CsgD, CsgA or CsgB inhibitor compound" refers to any compound able to prevent the action of curli, CsgD, CsgA or CsgB. The curli, CsgD, CsgA or CsgB inhibitor compound of the present invention is a compound that inhibits or reduces the activity of curli, CsgD, CsgA or CsgB. However, decreasing and/or reducing the activity of curli, CsgD, CsgA or CsgB can also be obtained by inhibiting curli, CsgD, CsgA or CsgB expression. The term "inhibiting curli, CsgD, CsgA or CsgB expression" means that the production of curli, CsgD, CsgA or CsgB in the bacteria after treatment is less than the amount produced prior to treatment. One skilled in the art can readily determine whether curli, CsgD, CsgA or CsgB expression has been inhibited in bacteria, using for example the techniques for determining curli, CsgD, CsgA or CsgB transcript level.

In a particular embodiment, the method of the present invention further comprises the step of applying at least one compound selected from CpxR, OmrA/B, McaS, RprA, and GcvB small oligonucleotide.

In a particular embodiment, the method of the invention further comprises the step of applying the nucleic acid sequence SEQ ID NO: 11.

In some embodiments, the method of the present invention further comprises the step of applying at least one antimicrobial agent.

The term "antimicrobial agent" has its general meaning in the art and refers to antibacterial agent, antiprotozoal agent or antifungal agent such as described in US2013/0029981. The antimicrobial agent may be a biocide, an antibiotic agent or another specific therapeutic entity. Suitable antibiotic agents include, without limitation, penicillin, quinoline, vancomycin, sulfonamides, ampicillin, ciprofloxacin, teicoplanin, telavancin, bleomycin, ramoplanin, decaplanin, and sulfisoxazole. Examples of antimicrobial agents include but are not limited to antibacterial agent, antiprotozoal agent or antifungal agent, a biocide, an antibiotic agent or another specific therapeutic agent. Suitable antibiotic agents include, without limitation, penicillin, quinoline, vancomycin, sulfonamides, ampicillin, ciprofloxacin, teicoplanin, telavancin, bleomycin, ramoplanin, decaplanin, and sulfisoxazole.

Typically, the oligonucleotide is applied to the surface using conventional techniques. Coating, dipping, spraying, spreading and solvent casting are possible approaches. More particularly, said applying is manual applying, applicator applying, instrument applying, manual spray applying, aerosol spray applying, syringe applying, airless tip applying, gas-assist tip applying, percutaneous applying, surface applying, topical applying, internal applying, enteral applying, parenteral applying, protective applying, catheter applying, endoscopic applying, arthroscopic applying, encapsulation scaffold applying, stent applying, wound dressing applying, vascular patch applying, vascular graft applying, image-guided applying, radiologic applying, brush applying, wrap applying, or drip applying.

In some embodiments, the method of the invention is particular suitable for preventing the development of bacteria growth on the surface and thus for preventing any contamination or infection that can be driven by said bacteria.

The oligonucleotide of the invention is particularly suitable in a method of preventing or treating biofilm formation in a subject in need thereof.

In some embodiments the "subject" denotes a mammal. In a preferred embodiment of the invention, a subject according to the invention refers to any subject (preferably human) afflicted with or susceptible to be afflicted with biofilm formation or infection from a biofilm.

Therefore, a further aspect of the invention relates to the oligonucleotide for use as a medicament.

The present invention also relates to a method of preventing or treating biofilm formation in a subject in need thereof comprising the step of administering to said subject a therapeutically effective amount of a oligonucleotide of the present invention.

The method of the invention may be performed for any type of biofilm formation such as subject undergoing surgery for chronic sinusitis, dental plaque, formation of dental plaque, gingivitis, legionellosis, urinary tract infections, catheter infections, middle-ear infections, coating contact lenses, endocarditis, infections in cystic fibrosis, and infections of permanent indwelling devices such as joint prostheses and heart valves.

In some embodiments, the method of the present invention is used in connection with a dental procedure. In one embodiment, the dental procedure is selected from the group consisting of an endodontic procedure such as a root canal, preparation for placement of a restorative material, and preparation for placement of a dental crown. In one embodiment, the method comprises, identifying a patient with a tooth that needs endodontic therapy. Then, the endodontic therapy is performed, such as for example removing some or all of the pulp of the tooth in the process of removing an infection. Next, the root canal is conventionally cleaned and shaped as well as filled following the obturation technique. After cleaning and shaping are done, and immediately before filling the root canal, the root canal system is irrigated with a composition comprising an amount of an oligonucleotide of the invention. In another embodiment, the method comprises, identifying a patient with a tooth that needs a dental procedure, such as for example a patient with a cavity prepared for placing a filing of a suitable material, such as for example amalgam, dental composites, glass ionomer cement, gold, or porcelain. Once the cavity has been prepared and is ready to be filled, the cavity is irrigated under isolation (rubber dam and clamp) with a composition comprising an amount of an oligonucleotide of the present invention. Then, the cavity is filled according to standard techniques. In another embodiment, the method comprises, identifying a patient with a tooth that needs a dental procedure, such as for example a patient prepared for placement of a dental crown. Next, the prepared tooth cavity is irrigated under isolation (rubber dam and clamp, or using high speed suction) with a composition comprising an amount of an oligonucleotide of the present invention, and the composition is allowed to contact the cavity and dry.

In a particular embodiment, oligonucleotides of the invention may be delivered in vivo alone or in association with a vector. In its broadest sense, a "vector" is any vehicle capable of facilitating the transfer of the oligonucleotide of the invention to the cells and enteric bacteria population. Preferably, the vector transports the nucleic acid to cells and enteric bacteria population with reduced degradation relative to the extent of degradation that would result in the absence of the vector. In general, the vectors useful in the invention include, but are not limited to, naked plasmids, non viral delivery systems (cationic transfection agents, liposomes, etc. . . . ), phagemids, viruses, other vehicles derived from viral or bacterial sources that have been manipulated by the insertion or incorporation of the oligonucleotide sequences. Viral vectors are a preferred type of vector and include, but are not limited to nucleic acid sequences from the following viruses: RNA viruses such as a retrovirus (as for example moloney murine leukemia virus and lentiviral derived vectors), harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus. One can readily employ other vectors not named but known to the art. In a preferred embodiment, the oligonucleotide sequence is under the control of a heterologous regulatory region, e.g., a heterologous promoter. The promoter can also be, e.g., a viral promoter, such as CMV promoter or any synthetic promoters.

In a particular embodiment, two or even more oligonucleotides can also be used at the same time; this may be particularly interesting when the oligonucleotides are vectorized within an expression cassette (as for example by U7 or U1 cassettes).

In one embodiment, the present invention relates to the oligonucleotide comprising or consisting of i) a nucleic acid sequence ranging from nucleic acid at position 1 to nucleic acid at position 24 in SEQ ID NO: 1, nucleic acid at position 1 to nucleic acid at position 24 in SEQ ID NO: 2, nucleic acid at position 1 to nucleic acid at position 23 in SEQ ID NO: 3, nucleic acid at position 1 to nucleic acid at position 24 in SEQ ID NO: 4, nucleic acid at position 1 to nucleic acid at position 23 in SEQ ID NO: 5, nucleic acid at position 1 to nucleic acid at position 23 in SEQ ID NO: 6, nucleic acid at position 1 to nucleic acid at position 21 in SEQ ID NO: 7, nucleic acid at position 1 to nucleic acid at position 22 in SEQ ID NO: 8, nucleic acid sequence SEQ ID NO: 10, or ii) a nucleic acid sequence having at least 70% of identity with the nucleic acid sequence ranging from nucleic acid at position 1 to nucleic acid at position 24 in SEQ ID NO: 1, nucleic acid at position 1 to nucleic acid at position 24 in SEQ ID NO: 2, nucleic acid at position 1 to nucleic acid at position 23 in SEQ ID NO: 3, nucleic acid at position 1 to nucleic acid at position 24 in SEQ ID NO: 4, nucleic acid at position 1 to nucleic acid at position 23 in SEQ ID NO: 5, nucleic acid at position 1 to nucleic acid at position 23 in SEQ ID NO: 6, nucleic acid at position 1 to nucleic acid at position 21 in SEQ ID NO: 7, nucleic acid at position 1 to nucleic acid at position 22 in SEQ ID NO: 8, nucleic acid sequence SEQ ID NO: 10 for use in a method of preventing or treating biofilm formation in a subject in need thereof.

In some embodiments, the present invention also relates to the oligonucleotide according to the invention for use in the prevention or treatment of bacterial infection in a subject in need thereof.

Compositions of the Invention

A further aspect of the present invention relates to a composition comprising an amount of an oligonucleotide.

In a particular embodiment, the composition of the present invention comprises an amount of an oligonucleotide which comprises or consists of:

i) a nucleic acid sequence ranging from nucleic acid at position 1 to nucleic acid at position 24 in SEQ ID NO: 1, nucleic acid at position 1 to nucleic acid at position 24 in SEQ ID NO: 2, nucleic acid at position 1 to nucleic acid at position 23 in SEQ ID NO: 3, nucleic acid at position 1 to nucleic acid at position 24 in SEQ ID NO: 4, nucleic acid at position 1 to nucleic acid at position 23 in SEQ ID NO: 5, nucleic acid at position 1 to nucleic acid at position 23 in SEQ ID NO: 6, nucleic acid at position 1 to nucleic acid at position 21 in SEQ ID NO: 7, nucleic acid at position 1 to nucleic acid at position 22 in SEQ ID NO: 8, nucleic acid sequence SEQ ID NO: 10, or ii) a nucleic acid sequence having at least 70% of identity with the nucleic acid sequence ranging from nucleic acid at position 1 to nucleic acid at position 24 in SEQ ID NO: 1, nucleic acid at position 1 to nucleic acid at position 24 in SEQ ID NO: 2, nucleic acid at position 1 to nucleic acid at position 23 in SEQ ID NO: 3, nucleic acid at position 1 to nucleic acid at position 24 in SEQ ID NO: 4, nucleic acid at position 1 to nucleic acid at position 23 in SEQ ID NO: 5, nucleic acid at position 1 to nucleic acid at position 23 in SEQ ID NO: 6, nucleic acid at position 1 to nucleic acid at position 21 in SEQ ID NO: 7, nucleic acid at position 1 to nucleic acid at position 22 in SEQ ID NO: 8, nucleic acid sequence SEQ ID NO: 10.

In some embodiments the composition is an antimicrobial composition.

The term "antimicrobial composition" refers to a composition that inhibits the biofilm formation induced by enteric bacteria. Typically the antimicrobial composition of the present invention is suitable for controlling biofilm formation, in thus for controlling and reducing bacterial growth and bacterial colonization.

In a particular embodiment, the present invention relates to the antimicrobial composition according to the invention which further comprises at least one compound selected from Hfq polypeptide, curli inhibitor compound, CsgD inhibitor compound, CsgA inhibitor compound, and CsgB inhibitor compound.

In a particular embodiment, the present invention relates to the antimicrobial composition according to the invention which further comprises at least one compound selected from CpxR, OmrA/B, McaS, RprA, and GcvB small oligonucleotide.

In a particular embodiment, the present invention relates to the antimicrobial composition according to the invention which further comprises the nucleic acid sequence SEQ ID NO: 11.

In some embodiments, the present invention relates to the antimicrobial composition according to the invention which further comprises at least one antimicrobial agent.

In some embodiments, the composition of the present invention is a pharmaceutical composition.

Typically the pharmaceutical composition of the present invention comprises pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, inhalation, sublingual, subcutaneous, intramuscular, intravenous, transdermal, local or rectal administration of the oligonucleotide, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, inhalation administration forms, aerosols, implants, subcutaneous, transdermal, topical, intraperitoneal, intramuscular, intravenous, subdermal, transdermal, intrathecal and nasal or intranasal administration forms and rectal administration forms.

Typically, the pharmaceutical compositions contain vehicles which are pharmaceutically acceptable for a formulation capable of being administered by nasal administration or by inhalation. Nasal administration may be under the form of liquid solution, suspension or emulsion. Solutions and suspensions are administered as drops. Solutions can also be administered as a fine mist from a nasal spray bottle or from a nasal inhaler. Inhalation may be accomplished under the form of solutions, suspensions, and powders; these formulations are administered via an aerosol, droplets or a dry powder inhaler. The powders may be administered with insufflators or puffers.

Pharmaceutical compositions of the present invention include a pharmaceutically or physiologically acceptable carrier such as saline, sodium phosphate, etc. The compositions will generally be in the form of a liquid, although this need not always be the case. Suitable carriers, excipients and diluents include lactose, dextrose, sucrose, sorbitol, mannitol, starches, gum acacia, calcium phosphates, alginate, tragacanth, gelatin, calcium silicate, microcrystalline cellulose, polyvinylpyrrolidone, celluose, water syrup, methyl cellulose, methyl and propylhydroxybenzoates, mineral oil, etc. The formulations can also include lubricating agents, wetting agents, emulsifying agents, preservatives, buffering agents, etc. Those of skill in the art will also recognize that nucleic acids are often delivered in conjunction with lipids (e.g. cationic lipids or neutral lipids, or mixtures of these), frequently in the form of liposomes or other suitable micro- or nano-structured material (e.g. micelles, lipocomplexes, dendrimers, emulsions, cubic phases, etc.).

One skilled in the art will recognize that the amount of an oligonucleotide or the antimicrobial composition to be administered will be an amount that is sufficient to induce amelioration of unwanted disease symptoms. Such an amount may vary inter alia depending on such factors as the gender, age, weight, overall physical condition, of the subject, etc. and may be determined on a case by case basis. The amount may also vary according to the type of condition being treated, and the other components of a treatment protocol (e.g. administration of other medicaments such as steroids, etc.). If a viral-based delivery of oligonucleotides is chosen, suitable doses will depend on different factors such as the viral strain that is employed, the route of delivery (intramuscular, intravenous, intra-arterial, oral, inhalation or other). Those of skill in the art will recognize that such parameters are normally worked out during clinical trials. In addition, treatment of the subject is usually not a single event. Rather, the oligonucleotides of the invention will likely be administered on multiple occasions, that may be, depending on the results obtained, several days apart, several weeks apart, or several months apart, or even several years apart.

Pharmaceutical compositions of the invention may include any further antimicrobial agent which is used in the treatment of biofilm formation or infection from biofilm formation. For example, pharmaceutical compositions of the invention can be co-administered with antimicrobial agent such as antibacterial agent, antiprotozoal agent or antifungal agent.

The invention also provides kits comprising at least one oligonucleotide or antimicrobial composition of the invention. Kits containing oligonucleotide or antimicrobial composition of the invention find use in therapeutic methods.

A further aspect of the invention relates to a material such as medical or industrial device (such as above described), characterized in that the oligonucleotide or the antimicrobial composition according to the invention is at least partly applied to said material.

The present invention relates to a method for screening a test substance useful for inhibiting or reducing the formation of a bacterial biofilm, comprising the steps of providing a host cell expressing CsgD, contacting the host cell with the substance, measuring the level of CsgD mRNA or protein after said contacting; and comparing the level of CsgD mRNA or protein after said contacting with a host cell not contacted with the agent; wherein a reduced level of the CsgD mRNA or protein after said contacting compared to the level of the CsgD mRNA or protein in the cell not contacted with the agent indicates that the agent inhibits the formation of a bacterial biofilm.

In some embodiments, the test substance is an oligonucleotide which is selected to hybridize to a CsgD nucleic acid sequence ranging from nucleic acid at position 128 to nucleic acid at position 151 in SEQ ID NO: 9, nucleic acid at position 128 to nucleic acid at position 149 in SEQ ID NO: 9, or nucleic acid at position 134 to nucleic acid at position 151 in SEQ ID NO: 9.

Oligonucleotide Sequences

SEQ ID NO: 1 for Salmonella Typhimurium RydC small RNA.
UUCCGAUGUAGACCCGUCCUCCUUCGCCUGCGUCACGGGUCCUGGUUAG

ACGCAGGCGUUUUCU

SEQ ID NO: 2 for Salmonella bongori RydC small RNA.
UUCCGAUGUAGACCCGCUCUUCUUCGCCUGCGUCACGGGUCUCAAUUAG

ACGCAGGCGUUUUCU

SEQ ID NO: 3 for Citrobacter koseri RydC small RNA.
UUCCGAUGUAGACCCGUUUCCUUCACCUGCGUCACGGGUCUGGUUACAC

GCAGGUGUUUUCU

SEQ ID NO: 4 for Escherichia coli RydC small RNA.
CUUCCGAUGUAGACCCGUAUUCUUCGCCUGUACCACGGGUCGGUUUUAG

UACAGGCGUUUUCU

SEQ ID NO: 5 for Shigella flexneri RydC small RNA.
UUCCGAUGUAGACCCGUAUUCUUCGCCUGUACCACGGGUCGGUUUAGU

ACAGGCGUUUUCU

SEQ ID NO: 6 for Escherichia fergusoni RydC small RNA.
UUCCGAUGUAGACCCGUAUGCUUCGCCUGCACCACGGGUCUGGUUAGGU

GCAGGCGUUUUAU

SEQ ID NO: 7 for Enterobacter aerogenes RydC small RNA.
UUCCGAUGUAGACCCACCUUUCACCUGCACUAUGGGUCUGGUUGCGUGC

AGGUGUCUUCU

SEQ ID NO: 8 for Klebsiella pneumonia RydC small RNA.
UUCCGAUGUUGGCCCGCCAGUUAACCUGCACGCCGGGCCUGUUUAGGUG

CAGGUUUUUCA

SEQ ID NO 9: X for Escherichia coli CsgD mRNA 5' domain.
GAUGUAAUCCAUUAGUUUUAUAUUUUACCCAUUUAGGGCUGAUUUAUU

ACUACACACAGCAGUGCAACAUCUGUCAGUACUUCUGGUGCUUCUAUUUU

AGAGGCAGCUGUCAGGUGUGCGAUCAAUAAAAAAAGCGGGGUUUCAUCAU

GUUUAAUGAAGUCCAUAGUAUUCAUGGUCAUACAUUAUUGUUGAUCACUA

AAUCUUCUUUGCAGGCG

SEQ ID NO: 10 for RydC 1-2tot that hybridizes to the CsgD mRNA sequence ranging from nucleic acid at position 134 to nucleic acid at position 151 in SEQ ID NO: 9.
AACATGATGAAACCCCGC SEQ ID NO: 11 for McaS oligonucleotide that hybridizes to the CsgD mRNA sequence ranging from nucleic acid at position 51 to nucleic acid at position 66 in SEQ ID NO: 9.
TGCACTGCTGCGTGTGTA SEQ ID NO: 12 for Escherichia coli RydC SEQ ID NO: 4 having an additional Uridin in the 3' end.
CUUCCGAUGUAGACCCGUAUUCUUCGCCUGUACCACGGGUCGGUUUUAG

UACAGGCGUUUUCUU

SEQ ID NO: 13 for Escherichia coli RydC H1.
CUUCCGAUGUAGACCCGUAUUCUUCGCCUGUACCUGCCCAGGGUUUUAG

UACAGGCGUUUUCUU

SEQ ID NO: 14 for Escherichia coli RydC H2.
CUUCCGAUGUACUGGGCAAUUCUUCGCCUGUACCACGGGUCGGUUUUA

GUACAGGCGUUUUCUU

SEQ ID NO: 15 for Escherichia coli RydC H3.
CUUCCGAUGUACUGGGCAAUUCUUCGCCUGUACCUGCCCAGGGUUUUA

GUACAGGCGUUUUCUU

The invention will be further illustrated by the following figures and examples. However, these examples and figures should not be interpreted in any way as limiting the scope of the present invention.

FIGURES

FIG. 1: RydC regulates biofilm synthesis in E. coli and S. enterica. A. Microtiter dish biofilm mass measured by crystal violet staining in Escherichia coli, Salmonella enterica (bongori), and Shigella sonnei after 48 h incubation. (left) The E. coli strains are wild-type MG1655Z1, its isogenic ΔRydC derivative (ΔRydC), strain containing a multicopy plasmid pUC18, and one containing pUC18 encoding RydC expressed from its endogenous promoter sequence (pUC18-rydC). (right) The same pUC18 constructs were added to Salmonella and Shigella. The data represent the means and standard deviations of at least ten replicates. B. RydC expression levels in the recombinant strains from the three bacteria monitored by northern blots on total RNAs directly extracted from the biofilms. 5S rRNAs are internal loading controls.

FIG. 2: RydC induction lowers curli synthesis by reducing CsgA and CsgB protein and mRNA levels in enteric bacteria. A. (left) Congo red (diazo dye) YESCA agar plates grown at 28° C. for 48 h added to Escherichia coli, Salmonella enterica (bongori) and Shigella sonnei. The experiments were repeated at least three times. The Shigella strain does not form curli because its csg locus is disrupted by insertions-deletions (20), an action considered to be an internal negative control. (right) The graph shows quantitation of curli formation in the four isogenic strains using the GelQuant.NET software (Arbitrary Units, AU). The data are derived from three independent experiments. B. Northern blots monitoring of 8-48 h of RydC expression in 'pUC18-rydC' isogenic strains, resulting in curli formations. As loading controls, the blots were also probed for 5S rRNA. C. Immunoblots with anti-CsgA and anti-CsgB antibodies showing CsgA and CsgB protein expression in an *E. coli* strain harbouring pUC18-rydC versus an isogenic strain containing the empty plasmid (*E. coli*+pUC18). Curli formation was a result of 8-48 h of incubation on YESCA agar plates at 28° C. for CsgA and 48 h for CsgB protein. The asterisks mark two aspecific protein bands, each revealed by one antibody. The graph shows CsgA protein quantification in the two isogenic strains (*E. coli*+pUC18 is blue; *E. coli*+pUC18-rydC is pink, Arbitrary Units, AU) relative to the levels of the aspecific protein. D. Northern blot analysis of the csgA and csgBA mRNAs in the two strains during curli formation at identical time points, as in panel A. The blots were also probed for tmRNA as loading internal controls. The graph shows csgA mRNA quantification in the strains relative to tmRNA (using a similar colour code as panel C).

FIG. 3: RydC lowers csgD mRNA and protein levels and the absence of endogenous levels of RydC increases csgD mRNA synthesis during curli formation. A. Immunoblots with anti-CsgD antibodies monitoring CsgD protein expression between 8 to 48 h curli formation on YESCA agar plates at 28° C. in an *E. coli* strain harbouring pUC18-rydC versus an isogenic strain containing the empty plasmid (*E. coli*+pUC18). The asterisk indicates an aspecific protein revealed by the antibody. The graph shows CsgD protein quantification in the two isogenic strains (*E. coli*+pUC18, top curve; *E. coli*+pUC18-rydC, down curve, Arbitrary Units, AU) relative to the amount of the aspecific protein. B. Northern blot analysis of the csgD and csgDEF mRNAs in the two strains during curli formation at time points, as in panel A. The blots were also probed for tmRNA as loading internal controls, The graph shows csgD mRNA quantification in the strains relative to tmRNA (similar code as in panel A, Arbitrary Units, AU). C. qPCR comparison of csgD mRNA expression in *E. coli* (white) and *E. coli*-ΔrydC (dark grey) strains during curli formation for 8 h on YESCA plates, normalized against the tmrna reference gene (Arbitrary Units, AU). The downregulation of csgD mRNA by RydC occurs after 4 h of incubation.

FIG. 4: Direct interaction between RydC and the csgD mRNA; ternary complex formation between RydC Hfq and its mRNA target. A. Schematic representation of the csgD mRNA 5'-domain emphasizing three RNA constructs. csgD mRNA$_{215}$ corresponds to the 215 nucleotides from the 5'-end of the mRNA, emphasizing the SD and AUG translation initiation signals. In the csgD mRNA$_{100}$ variant, 115 nucleotides from the csgD mRNA 5'-end were deleted. The 5'-UTR of the csgD mRNA (the sequence between the black brackets) was deleted in mutant csgD mRNA$_{\Delta 5'UTR}$, therefore starting at G$_{+3}$. B. Complex formation between RydC and each of the three csgD mRNA constructs. Native gel retardation assays of purified labeled RydC with increasing amounts of purified, unlabelled csgD mRNA$_{215}$, csgD mRNA$_{100}$, or csgD mRNA$_{\Delta 5'UTR}$ are shown. The csgD mRNA construct/RydC molar ratios are indicated below each lane. Competition assays were performed with a 100-fold molar excess of unrelated, purified SprD RNA (18) in the presence of each of the csgD mRNA$_{215}$ and csgD mRNA$_{100}$ constructs. C. Ternary complex formation between RydC, csgD mRNA$_{215}$, and Hfq. Left panel: Native gel retardation assays show complex formation between labelled RydC and increasing amounts of unlabelled csgD mRNA$_{215}$ (at a 1- to 50-fold excess as compared with RydC) in the presence or absence of purified Hfq. Hfq is at a 1:1 molar ratio with RydC. The asterisks indicate the 'RydC*/csgD mRNA' molar ratio used to perform the competition assays with a 10- to 100-fold molar excess of unlabelled RydC. Right panel: csgD mRNA$_{215}$ interacts with Hfq in the absence of RydC in vitro. Hfq is at a 20:1 molar ratio with the mRNA. Note that the csgD mRNA adopts two conformations on a native gel.

FIG. 5: Hfq and RydC both prevent ribosome loading onto the csgD mRNA. A. Ribosome toeprint assays performed on csgD mRNA$_{215}$ in the presence of increasing amounts of RydC or purified Hfq. Left panel: 25- to 200-fold excess RydC as compared to csgD mRNA$_{215}$. Right panel: 0.4- to 4-fold excess purified Hfq as compared to csgD mRNA$_{215}$. The experimentally-proven toeprints are indicated with asterisks, with their sizes reflecting the intensity of the toeprints. +/−, indicates the presence of purified ribosomes with the csgD mRNA; U, A, G, and C: indications of the csgD mRNA$_{215}$ sequencing ladders. The SD sequence and AUG initiation codon of the csgD mRNA$_{215}$ are also indicated. B. Schematic representation of the csgD mRNA 5'-domain, emphasizing the location of the ribosome toeprints (marked with asterisks) induced by either Hfq or RydC.

FIG. 6: Structural probing and deletion analysis of the interaction between RydC and csgD mRNA. A. SEQ ID NO: 9, Secondary structure of the csgD mRNA$_{215}$ 5'-end (nucleotides −146 to +69) from *E. coli* with the structural changes in the csgD mRNA induced by RydC. This is based on structural probes in solution (FIG. S2), which provide experimental support for the proposed structure. Triangles are V$_1$ cuts; arrows capped by a circle are S$_1$ cuts; plain arrows are lead cleavages. Cleavage intensity is shown with filled (strong cuts) or open (weaker) symbols. Structural domains (H1-H9, L1-L8) are indicated. Most of these changes are clustered onto L6-H6 and H7-L7. Nucleotides from the csgD mRNA proposed to interact with RydC are in bold (for details, see FIG. 7). B. SEQ ID NO: 12, RydC secondary structure (4) emphasizing the nucleotides (nts) from its 5'-domain (in bold) interacting with the csgD mRNA. The structure is based on probing (FIG. S3) and mutational analysis (panel E and FIG. 7). Structural changes induced by the binding of csgD mRNA with RydC are clustered on S1-H1-L1. Only the structural changes induced by duplex formation are indicated here, using the same indicators as in section A. C. Proposed antisense pairing between RydC (nucleic acids at position 3 to 24 of SEQ ID NO: 4 and SEQ ID NO: 12) and the csgD (nucleic acids at position 127 to 151 of SEQ ID NO: 9) mRNA leads to the sequestration of the mRNA ribosome binding site (outlined) by the RydC 5'-domain. Pairing interactions between RydC and the csgD mRNA are based on native gel retardation assays, deletion analysis, and structural mapping of RydC in complex with the csgD mRNA. Only the structural data concerning the RNA duplex conformation is indicated, with the same symbols as FIG. 6A. The plus (+) and minus (−) signs indicate the appearance or disappearance of cleavages induced by structural probes when the two RNAs are respectively in duplex D. RydC binding does not require 115 nts from the csgD mRNA 5'-end. Schematic representation of the csgD mRNA 5'-domain, emphasizing the csgD mRNA$_{115}$ construct (in grey), which lacks the H6-H9 domains (dotted lines). The grey bracket delineates the shorter csgD mRNA$_{115}$ construct. Native gel retardation assays of purified labelled RydC with increasing amounts of csgD mRNA$_{115}$ (125- to 250-fold excess relative to RydC) show that the first 115 nts from the csgD mRNA 5'-end are unable to interact with RydC. This result is in agreement with the probing data, which reveal a lack of structural changes in this area of the mRNA when in complex with RydC. E. Native gel retardation and in vitro translation evidence that the RydC 5-domain interacts with and controls CsgD translation. Left panel: Schematic representation of RydC, emphasizing the RydC$_{A5'}$ construct (in black), which lacks the S1-H1-L1 5' domains (in grey). Right panels: A 250-fold excess of synthetic, purified RydC$_{A5'}$ is unable to bind with csgD mRNA$_{215}$, whereas wild-type RydC can (FIG. 4B). In vitro translation of csgD mRNA$_{215}$ in the presence of RydC$_{A5'}$ at a 50-fold molar ratio with the csgD mRNA, showing that the RydC 5'-domain S1-H1-L1 is essential in lowering CsgD translation. The lack of RydC$_{A5'}$ activity is due to its incapacity to interact with the csgD mRNA, as evidenced by the absence of complex formation (upper panel).

FIG. 7: The interaction between Hfq and csgD mRNA, the role of Hfq in translational regulation, and the inverse correlation between RydC and csgD mRNA expression during curli formation in vivo. A. SEQ ID NO: 9, Secondary structure of csgD mRNA$_{215}$, with the structural changes induced by Hfq on the csgD mRNA conformation. This model is based on structural probing of the RNA-protein complex in solution (FIG. S4). The plus (+) and minus (−) signs indicate the appearance or disappearance of cleavages induced by the structural probes when the protein is in complex with the mRNA. B. RydC mutants, with mutated nucleotides in bold: disrupted stem H1 (SEQ ID NO: 13, RydC$_{H1}$); stem H1 and the interacting sequence with the csgD mRNA (SEQ ID NO: 14, RydC$_{H2}$); and a compensatory mutant which restores the H1 structure (SEQ ID NO: 15, RydC$_{H3}$). C. In vitro translation of csgD mRNA$_{503}$ in the presence of various RydC mutants, with and without a 2-fold molar excess of Hfq. The translation products arbitrarily set to 1 were quantified relative to csgD mRNA$_{503}$ translation in the absence of RydC and Hfq (upper lane). To explore the effect of RydC in the presence of Hfq, the translation products were also set to 1 and quantified relative to CsgD translation in the presence of Hfq (lower lane), tmRNA was used as an internal negative control. D. qPCR monitoring of csgD mRNA and RydC expression in *E. coli* cells during curli formation on YESCA plates, normalized against the tmrna reference gene.

FIG. 8: Schematic integration of protein and RNA regulators of CsgD expression, colocalization of the binding sites of the 6 sRNAs regulating this expression, and the Hfq-induced mRNA structural changes. A. The proteins and sRNAs (16) that control CsgD expression in response to various specific environmental changes that trigger cell adhesion and biofilm formation. The black arrows and bars indicate positive and negative regulations, respectively. Endogenous levels of RydC induce positive regulations of the Yej operon (4) and of CFA synthase expression (8). The various environmental triggers that influence and initiate these regulations are in italics, the ultimate effector molecule being the CsgD transcription factor. B. The binding sites of the six sRNAs that reduce CsgD translation initiation are indicated on the csgD mRNA 5' platform. OmrA/B, GcvB, McaS, RprA, and RydC (Bordeau V, Felden B. Curli synthesis and biofilm formation in enteric bacteria are controlled by a dynamic small RNA module made up of a pseudoknot assisted by an RNA chaperone. Nucleic Acids Res. 2014 April; 42(7):4682-96). The asterisks indicate the csgD mRNA domains from that are subjected to reactivity changes in the presence of Hfq, which strikingly match the sRNA binding sites.

EXAMPLES

Example 1

Material & Methods

Bacterial Strains, Media and Growth Conditions

*E. coli* K-12 MG1655Z1, *S. sonnei* and *S. enterica* strains and their derivatives were used (Table S1). RydC gene disruption and overexpression in *E. coli* cells were done as previously described (4). The biofilm assays were performed in 96-well polystyrene plates, as previously described (18). *E. coli*, *S. enterica*, and *S. sonnei* cells were grown aerobically under static conditions at 28° C. in half-diluted M9 media supplemented with a 0.4% glucose carbon source. After 48 h growth, planktonic cells were discarded and kept for growth evaluation at OD$_{600\,nm}$. Each well was washed twice with PBS and put into a 'swimming pool', pooled with the initial supernatant. Biofilm was developed in plates then dyed with crystal violet for 15 min at room temperature. The biofilm was recovered through application of an 80% absolute ethanol and 20% acetone solution and by pipetting up and down. After 2 further washes in 'ethanol/acetone', the number of surface-attached bacteria was estimated from the optical density at 590 nm and divided by the evaluation of growth at 600 nm. Curli expression was monitored for 48 h at 28° C. on Congo red plates (1% Casamino acids, 0.1% yeast extract, 20 μg ml$^{-1}$ Congo red and 10 μg ml$^{-1}$ Coomassie Brilliant Blue G). Expression of csg proteins and csg genes was accomplished by growing cells on YESCA agar (1% Casamino acids, 0.1% yeast extract and 2% agar) at 28° C. and for various time frames. When required, the growth media were supplemented with spectinomycin (10 μg ml$^{-1}$) or ampicillin (50 μg ml$^{-1}$).

Northern Blots and Quantitative RT-PCR Experiments

After 8, 10, 15, 24, and 48 h incubation at 28° C. on YESCA plates, cells were scraped with fresh ethanol containing 5% phenol and immediately centrifuged for 10 min at 4500 rpm at 4° C. Total RNA extraction was performed on the cell pellet by the hot acid phenol method as described previously (4). For csgD and csgA mRNA analysis, 20 μg total RNA was fractionated by 1% agarose gel containing 2.2 M formaldehyde, then transferred onto nylon membranes (Zeta-Probe GT, Bio-Rad) using a Vacuum Blotter (Bio-Rad) as per the manufacturer's protocol. For RydC analysis, northern blot analysis was carried out by loading 10 μg total RNA per lane onto a 5% PAGE containing 8M urea. The gel was then electroblotted in 0.5×TBE onto nylon membrane (Zeta-Probe GT) at 30V for 1 h 30. Prehybridization and hybridization were performed in ExpressHyb (Clontech). CsgD mRNA, csgA mRNA, RydC, tmRNA, and 5S rRNA were analysed using 5' end-labelled DNA oligonucleotides (Table S2). Signals were detected using a PhosphorImager and quantified using ImageQuant NT 5.2 (both from Molecular Dynamics). CsgD mRNA and RydC expression levels in the *E. coli* strains were monitored by quantitative PCR. After an overnight culture in YESCA broth and then incubations for 2, 4, and 8 h on YESCA plates at 28° C., total RNA were extracted as described for the northern blots. The cDNAs were produced using a High-Capacity cDNA Reverse Transcription Kit (Applied Biosystems).

RT-PCR was performed using RealMasterMIX SYBR kit (5'PRIME) on a StepOnePlus Real-Time PCR (Applied Biosytems). Using the comparative ΔΔCt method, the amount of csgD mRNA was normalized against the tmrna reference gene.

Western Blots

After 8, 10, 15, 24, and 48 h incubation at 28° C. on YESCA plates, cells were scraped with PBS and immediately centrifuged for 10 minutes at 4500 rpm at 4° C. Cell pellets were then treated with formic acid in ice during 5 minutes. After evaporation in Speedvac, each pellet was dissolved in sample loading buffer (Laemmli 1× with 10% β-mercaptoethanol) and heated at 90° C. for 5 min. Samples were separated onto 15% SDS-PAGE gels and transferred to PVDF membranes (GE Healthcare) at 100 volts for 1 h. Membranes were blocked in TBS containing 5% milk. Incubation with primary antibodies was performed for 2 h at room temperature at a 1:1000 dilution for anti-CsgA and at 1:5000 for anti-CsgD. After the incubation with the secondary antibody for 2 h at room temperature, the blots were washed in TBS containing 0.05% Tween, and then developed in ECL Western Blotting Detection Reagent (GE Healthcare). Results were obtained by exposing the blots with an ImageQuant LAS 4000 (GE Healthcare) for incremental incubation times. The signals were quantified using Image-Quant NT 5.2.

In Vitro Transcription, Purification and Ends Labelling

To generate the various csgD mRNA fragments as well as the sRNA's RydC, DNA templates containing a T7 promoter sequence were generated by PCR using the appropriate primers (Table S2) followed by in vitro transcription using a MEGAscript kit (Ambion) per the manufacturer's protocol. Transcription products were then electrophoresed onto a 6% PAGE containing 8M urea, excised from the gel, then precipitated and after elution from the gel and ethanol. When necessary, purified RNA was dephosphorylated using CIP (New England Biolabs), 5'end-labelled with ATP $\gamma$-$^{32}$P (PerkinElmer) and T4 polynucleotide kinase (NE Biolabs), then treated with gel purification, passive elution, and ethanol precipitation.

Structural Analysis of RNAs

Structural analysis of end-labelled and gel-purified csgD mRNA or RydC was performed as described previously (4). 2 pmol of 5' end-labelled csgD mRNA was mixed with 100 pmol of cold RydC or 40 pmol of Hfq and incubated 30 or 10 min at 37° C., respectively. After the incubation, $V_1$ ($5.10^{-5}$ or $15.10^{-5}$ unit), $S_1$ (0.5, 1 or 2 units), or lead acetate (0.5 or 1 mM final) were added and the mixes were incubated for 10 min more at 37° C. The reactions were precipitated and the pellets dissolved in loading buffer (Ambion). Samples were loaded onto an 8% PAGE containing 8M urea. Gels were dried and visualized (PhosphorImager).

Hfq Purification

Hfq was purified as previously described (4). E. coli BL21(DE3) harbouring the pTE607 plasmid and grown at 37° C. to an $OD_{600}$ of 0.4. After induction with 1 mM IPTG during 3 hours, cells were pelleted, dissolved in a buffer solution (20 mM Tris-HCL, 500 mM NaCl, 10% glycerol, and 0.1% Triton X-100), sonicated, heated at 80° C. for 10 min, and finally centrifuged. Supernatant was then charged onto an 'AKTA purifier' (GE Healthcare) equipped with a $Ni^{2+}$ column. Washes were performed with buffer containing 10 mM imidazole; the Hfq protein was eluted with the same buffer but with 300 mM imidazole. The purity of the protein was visualized on a 12% SDS-PAGE and concentration estimated by Bradford assay.

Toeprint and Gel Shift Assays

After denaturation followed by renaturation at room temperature, annealing mixes containing 0.2 pmol csgD mRNA and 1 pmol of labelled primer were incubated for 15 min with or without various concentrations of RydC or Hfq. fMet-tRNA$^{fMet}$ was then added for 5 min. Reverse transcription was started by adding 2 μL of AMV RT (NE Biolabs) and dNTPs for 15 min, then stopped by adding 10 μL of Buffer II (Ambion). The cDNAs and sequencing reactions were run on polyacrylamide gels, and signals detected using a PhosphorImager. Gel retardation assays are performed as previously described (4). 0.5 pmol of labelled RydC were incubated for 10 min at 37° C. with various concentrations (0-500 pmols) of unlabelled csgD mRNA$_{215}$, csgD mRNA$_{\Delta 5'UTR}$, or csgD mRNA$_{100}$ in 1×TMN buffer (20 mM Tris-acetate pH 7.6, 100 mM sodium acetate, and 5 mM magnesium acetate). Samples were loaded onto a native 5% acrylamide gel and separated with 0.5×TBE at 4° C. Gels are dried and visualized (PhosphorImager).

In Vitro Translation Assays

In vitro translation of CsgD mRNA$_{503}$ (2.5 pmols) using [$^{35}$S]-methionine was carried out with a PURESYSTEM (Cosmo Bio) following the manufacturer's instructions and as described previously (13). After RNA denaturation for 2 min at 85° C., chilling 2 min on ice, then renaturation for 5 min at 37° C. in TMN 1× buffer, a pre-complex between RydC and 10 pmol of Hfq was performed during 10 minutes at 37° C. To form the complex with the csgD mRNA, we again incubated for 10 min at 37° C. then translation assays were initiated by adding [$^{35}$S]-methionine and the PURESYSTEM classic II. Each reaction was denatured in a 1× Laemmli buffer at 95° C. for 5 min, loaded onto a 16% Tris-glycine gel, and visualized on a PhosphorImager.

Results

RydC induction reduces biofilm formation in two enteric bacteria. Bacterial sRNAs often regulate the expression of several targets (1). To search for a phenotype associated with the expression of RydC, E. coli strains either deficient in RydC expression (ΔRydC) or harbouring a multicopy plasmid stimulating RydC expression were used. Interestingly, a 'RydC-dependent' biofilm phenotype was detected. After 48 hours incubation at 28° C., in both E. coli and S. enterica, increasing RydC expression reduces biofilm formation by about one-third and one-half respectively when compared with isogenic strains (FIG. 1A). The ΔRydC E. coli strain essentially forms biofilms in the same way the wild-type (wt) strain (FIG. 1A). In the closely-related Shigella genus, biofilm formation is impaired by mutations in the curli gene locus (20). Accordingly and irrespective of RydC, S. sonnei bacteria neither synthesise curli nor produce biofilms. Total RNAs were extracted from the biofilms and RydC levels were monitored by northern blots (FIG. 1B). In the E. coli and S. enterica cells, RydC expression is low, probably after reduction by unknown factors to facilitate biofilm synthesis. This could explain the absence of phenotypic differences between the wt and ΔrydC E. coli strains. In the three enteric bacteria transformed with pUC-rydC, RydC induction was verified during biofilm formation (FIG. 1B). It can be concluded that stimulation of RydC expression reduces biofilm formation in E. coli and S. enterica.

RydC lowers curli synthesis by reducing CsgA and CsgB protein and mRNA levels. In enteric bacteria, curli fibres are involved in surface adhesion, cell aggregation, and biofilm formation (21). One possible explanation for the involvement of RydC in *E. coli* and *S. enterica* biofilm formation might be linked to curli biogenesis. Curliated bacteria stain red when grown on YESCA plates supplemented with Congo Red (CR) diazo dye (23). After 48 hours incubation at 28° C., stimulating RydC expression results in lowered curli formation in *E. coli* and *S. enterica* cells (FIG. 2A). The ΔrydC *E. coli* strain forms consistently slightly more curli than isogenic cells (FIG. 2A, right panel). During curli synthesis on YESCA plates with a RydC-overproducing strain, RydC gradually accumulates up to 15 hours and remains high afterwards (FIG. 2B). In *E. coli*, at least six proteins encoded by the csgBA and csgDEFG operons are dedicated to curli formation (23). Homologous agfBA and agfDEFG operons were also identified in *Salmonella* (22). In *E. coli*, csgBA encodes the two curli structural subunits (24): CsgA is the major structural subunit whereas CsgB is a nucleator. To determine whether RydC influences csgBA expression in *E. coli*, the effect of RydC accumulation on steady state levels of the CsgA protein was monitored by western blots using anti-CsgA antibodies at several time points (0-48 hours) during curli formation on YESCA plates. CsgA had a similar overall profile in a wt strain transformed with an empty vector as that of cells overexpressing RydC. CsgA is detected after 10 h incubation, increases up to 24 hours, and then decreases (FIG. 2C). However, western blots show that stimulating RydC expression reduces the quantity of the CsgA structural protein by up to 2.5 times as compared to the wt (FIG. 2C). After 24 h incubation, RydC induction strongly reduces CsgA levels. CsgB expression was also monitored after 48 h by western blots using anti-CsgB antibodies. Compared to an isogenic strain, promoting RydC expression also reduces the CsgB nucleator protein by about two-fold (FIG. 2C).

CsgA and CsgB proteins are produced from a single operon and their RydC-induced reduction could originate from an mRNA-level regulation. Using a DNA probe targeting the csgA mRNA, two ~0.65- and ~1.15 kb-long transcripts were detected in the wt and RydC-overproducing strains by northern blots (FIG. 2D), and these correspond respectively to the csgA and csgBA mRNAs (25). In the wt cells, the two mRNAs are detected early, and as expected their highest expression is around 15 hours before optimal expression of the CsgA protein (FIG. 2C), decreases thereafter, and is undetectable after 48 h (FIG. 2D). During curli synthesis, after 10 h incubation high levels of RydC decrease the steady state levels of csgBA and csgA mRNA transcripts by half. The stronger reduction of csgBA mRNA expression in the RydC-overproducing strain occurs after 15 h incubation. Thus, the maximum reduction of csgBA mRNA expression in the RydC-overexpressing strain occurs when RydC expression is highest (FIG. 2B). In both strains, there is a 9 h interval between the peaks of csgA transcription and translation, which could be ascribed to unknown CsgA regulators acting at the post-transcriptional level. Additional time points between 15 and 24 h would be required to investigate this further. In summary, RydC induction impairs curli synthesis by lowering CsgA and B, mRNA, and protein levels, in turn reducing biofilm formation.

RydC controls CsgD protein and mRNA expression levels. CsgD is a transcriptional activator of the csgBA operon required for curli and biofilm synthesis in *E. coli* (23). To assess whether RydC influences CsgD expression in *E. coli*, the effect of RydC expression on steady state levels of the CsgD protein was monitored by western blots using anti-CsgD antibodies at several times during curli synthesis on YESCA plates (FIG. 3A). CsgD protein expression was detected after 8 h incubation and increased to a maximum at 15 hours, which as expected for a csgBA transcriptional activator corresponds to the peak of csgBA mRNA expression (FIG. 2D), then slowly decreased down to zero after 48 h. This indicates that curli formation is substantially induced after 15 h incubation in *E. coli*. Compared to an isogenic strain, at all times during curli synthesis, induction of RydC expression reduced the CsgD protein up to five-fold (FIG. 3A). Thus, RydC impairs curli and biofilm synthesis by lowering CsgD protein levels. RydC may regulate CsgD expression at the mRNA level. During curli formation, RydC involvement in csgD mRNA levels was monitored by northern blots using a DNA probe specific for csgD mRNA. Hybridization of total RNAs extracted from curli-producing cells identified two ~0.9- and ~1.6 kb-long transcripts (FIG. 3B), compatible respectively with the csgD and csgDEF mRNAs (23). The highest expression of the two mRNAs is at about 10 h, then it decreases to nothing after 48 h (FIG. 3B). During curli formation, the csgD mRNA and protein expressions peak before that of csgBA mRNA and proteins, which is as expected for a transcriptional regulator when compared to its target genes. Throughout curli synthesis, inducing RydC expression reduces the csgD mRNA steady state levels down to half when compared to the isogenic strain. There is about a 5 h gap between the peaks of csgD transcription and translation which might be ascribed to previously-reported or unknown regulators of csgD expression acting at the post-transcriptional level. Additional time points between 10 and 15 h would be required to further investigate this observation. Compared to an isogenic strain, the lack of endogenous levels of RydC increases csgD mRNA synthesis about three-fold after 8 h of curli formation on YESCA plates (FIG. 3C). This result demonstrates the negative influence of RydC on csgD mRNA steady state levels in vivo. RydC reduces biofilm formation by impairing curli synthesis through lowering of CsgD protein and mRNA levels, in turn decreasing CsgA mRNA and CsgA and CsgB protein levels.

CsgD expression reduction by RydC interaction with csgD mRNA and the influence of the mRNA 5'UTR in complex formation. RydC controls csgD mRNA expression either indirectly via dedicated regulators or directly by antisense pairings with the mRNA. The CsgDEFG mRNA transcriptional start site was mapped by primer extension analysis, and is located 146 nts upstream from the CsgD initiation codon (23). Gel retardation assays were used to analyse duplex formation between RydC and a 215 nts-long csgD mRNA fragment (mRNA$_{215}$). mRNA$_{215}$ contains the 5'UTR sequence (146 nts) followed by 69 nts corresponding to the first 23 codons from its coding sequence (FIG. 4A). An 'RydC-csgD mRNA$_{215}$' duplex was detected (FIGS. 4B and S1) and its binding is specific, as a 100-fold molar excess of unrelated RNA (SprD) does not remove the csgD mRNA$_{215}$ from its preformed 'RydC-csgD mRNA$_{215}$' complex. To test the importance of the csgD mRNA 5'-UTR in the binding of RydC, a csgD mRNA deletion mutant lacking the 5'-UTR and starting at $G_{+3}$ was constructed (mRNA$_{\Delta 5'UTR}$). mRNA$_{\Delta 5'UTR}$ does not interact with RydC (FIG. 4B), demonstrating that the csgD mRNA 5'-UTR is essential for binding. Is the entire 5'-UTR of csgD mRNA required? To see if this is so, a second mutant (mRNA$_{100}$) was made containing 31 nts from the csgD mRNA 5'UTR including the TIS, followed by 69 nucleotides from its coding sequence. A 'RydC-csgD mRNA$_{100}$' duplex was detected (FIGS. 4B and S1), and the binding was specific since a 100-fold molar excess of unrelated RNA (SprD) did not remove the csgD mRNA$_{100}$ from its preformed 'RydC-csgD mRNA$_{100}$' complex. The binding ability of mRNA$_{100}$ with RydC was lower than that with mRNA$_{215}$ (FIG. 4B and S1), suggesting structural differences between these mRNAs (see below), or a lower affinity between RydC and mRNA$_{100}$ as compared to that with mRNA$_{215}$. Our results demonstrate that RydC forms a stable complex with the csgD mRNA in vitro and that at least a section of its 5'UTR, including the TIS, is required for binding.

Hfq facilitates the interaction between RydC and the csgD mRNA. RydC interacts with Hfq in vitro, and the protein considerably enhances RydC stability in vivo (4). Therefore, Hfq may facilitate the pairings between RydC and csgD mRNA. To test this, gel retardation assays were performed between labelled RydC, purified E. coli Hfq (1:1 molar ratio relative to RydC), and increasing concentrations of unlabelled csgD mRNA$_{215}$. An 'RydC-Hfq-csgD mRNA$_{215}$' ternary complex is detected (FIG. 4C, left), and nearly all of the RydC is in the complex at a one-to-one molar ratio with csgD mRNA$_{215}$. In the absence of Hfq, to obtain about half the amount of RydC in complex with its target, there is a need for a 1000-fold molar excess of csgD mRNA$_{215}$ versus RydC (FIG. S1). This also indicates that RydC and csgD mRNA$_{215}$ can simultaneously interact with Hfq. In the absence of RydC, Hfq interacts with the csgD mRNA$_{215}$ in vitro (FIG. 4C, right). Hfq facilitates the interaction between RydC and the csgD mRNA, improving the efficiency of the regulation.

The csgD mRNA ribosome binding site is sequestered by RydC and by Hfq to prevent translation initiation. Since the interaction of RydC with the csgD mRNA requires the 31 nts upstream from the initiation codon that contain the TIS, RydC could prevent ribosome loading onto the csgD mRNA. To test this, toeprint assays were performed on ternary initiation complexes, including purified ribosomes, initiator tRNA$^{fMet}$, and the csgD mRNA$_{215}$. A strong ribosome toeprint was detected at position $C_{+15}$ on csgD mRNA$_{215}$, 14 nts downstream from $A_{+1}$ of the initiation codon (FIG. 5A, left). Minor toeprints were also detected upstream, at positions $A_{+22}$ and $A_{+26}$, suggesting some degree of freedom in the positioning of the ribosome onto csgD mRNA$_{215}$, or else a structural rearrangement of the mRNA upon ribosome binding. In the absence of Hfq, RydC reduced ribosome loading onto the csgD mRNA in a concentration-dependent manner, requiring elevated amounts of sRNA for the regulation (FIG. 5A, left). In the absence of RydC, low amounts of purified Hfq also prevent csgD mRNA translation initiation (FIG. 5A, right). Thus both Hfq alone or elevated amounts of RydC have the ability to reduce CsgD translation initiation in vitro.

Monitoring the CsgD mRNA conformation by structural probes. As a prerequisite, conformations of free csgD mRNA$_{215}$ and free csgD mRNA$_{100}$ were investigated in solution. Both transcripts were end-labelled and their solution structures were probed by RNase $V_1$, which cleaves double-stranded (ds) RNAs or stacked nucleotides, and by nuclease $S_1$ and lead, which both cleave accessible single-stranded (ss) RNAs. The reactivity toward these structural probes was monitored for each nucleotide (FIG. S2 for csgD mRNA$_{215}$ and FIG. S3 for csgD mRNA$_{100}$). The data are summarized onto the supporting model of csgD mRNA$_{215}$ (FIG. 6A) and csgD mRNA$_{100}$ (FIG. S3). For csgD mRNA$_{215}$, the data showed the existence of nine folded helices (H1-H9, with $V_1$ cuts and without lead or S1 cleavages), all of which except H3 and H9 are capped by loops (presenting $S_1$ and lead cleavages but no $V_1$ cuts). An internal bulge between H4 and H5 was revealed by numerous $S_1$ cuts at $G_{-62}$-$U_{-65}$. Structural analysis of the csgD mRNA is consistent with a previous RNase $T_1$ and lead analysis (13) that proposed the existence of SL1 (H4-H5) and SL2 (H7). However our data suggests the existence of additional helices (H1-H3, H6, H8-H9; FIG. 6A) that may not be conserved (13). Probing data indicates that the beginning of the csgD mRNA coding sequence is tightly folded and embedded within four helices (H3, H7-H9). The conformation of csgD mRNA$_{100}$ was monitored by structural probes (FIG. S3), and these data were compatible with the existence of H7 and H8. In that shorter mRNA fragment, however, the conformation of its 5'- and 3'-ends is different than that of csgD mRNA$_{215}$: it lacks H6 and H9 but has an additional helix (H10) that bridges the 5'- and 3'-ends (FIG. S3). H7, H8 and H10 are joined by three accessible ss RNAs ($U_{-25}$-$A_{-14}$, $A_{+22}$-$A_{+26}$, and $C_{+50}$-$U_{+60}$).

Monitoring the RydC-CsgD mRNA' complex by structural probes. Structural changes induced by RydC complex formation were examined by subjecting the 'RydC-csgD mRNA$_{215}$' and 'RydC-csgD mRNA$_{100}$' complexes to nuclease $S_1$, RNases $V_1$, and lead statistical digestions. Binding of RydC induced a cluster of structural changes located in a similar, restricted region within the two csgD mRNA constructs encompassing the SD and AUG sequences, from $A_{-20}$ to $G_{+3}$ (FIGS. 6A, S2, and S3). When RydC interacts with csgD mRNA$_{215}$, the sRNA pseudoknot undergoes structural changes at its 5'-end that includes S1, H1, and L1 (FIGS. 6B and S2), as a result of which S1 and L1 should become double stranded. The structural data supports a model of interaction between csgD mRNA and RydC in which 'L6-H7-L7' from the mRNA (including the TIS) pairs with 'S1-H1-L1' from RydC (FIG. 6C). To provide additional experimental evidence for the proposed pairing model, a csgD mRNA mutant lacking H6-H9 was engineered and produced (csgD mRNA$_{115}$, FIG. 6D). Based on the probing data and pairing model, it should not be able to bind RydC. Indeed, when csgD mRNA$_{215}$ was in complex with RydC, there were no structural modifications at the first 115 nts from the csgD mRNA 5'-end (FIGS. 6A and S2). CsgD mRNA$_{115}$ did not interact with RydC, even when at a 250-fold excess (FIG. 6D), indicating that the recognition domains of csgD mRNA for binding RydC are not in the first 115 nts from the mRNA leader region. Conversely, a RydC mutant lacking 'S1-H1-L1' was constructed (RydC$_{\Delta 5}$', FIG. 6E), and gel retardation assays with csgD mRNA$_{215}$ revealed the absence of complex formation between the two RNAs (FIG. 6E, right). Translation assays provide direct experimental evidence that, unlike wt RydC, RydC$_{\Delta 5}$' was unable to reduce csgD mRNA translation (FIG. 6E, right).

Hfq induces a conformational rearrangement of the csgD mRNA. Structural changes induced by complex formation between Hfq and the csgD mRNA were examined by subjecting an 'Hfq-csgD mRNA$_{215}$' complex to nuclease $S_1$, RNases $V_1$, and lead statistical digestions (FIG. S4). Binding of Hfq induced a cluster of structural changes on the csgD mRNA at loops L4, L4-5, L5, and L6, all of which became protected against lead and $S_1$ cuts (FIGS. 7A and S4). This provides direct evidence for structural modifications of the csgD mRNA 5'-UTR. Hfq also induced reactivity changes within the csgD mRNA coding sequence, especially within helices H7 and H8 (FIG. 7A). This indicates that Hfq induced a significant conformational rearrangement of the csgD mRNA 5'-UTR, including part of its actual coding sequence.

Evaluation of the involvement of the RydC structure and pairings in regulation of csgD mRNA translation. According to the probing data and the RNA deletion mutants (FIG. 6), one can predict that the RydC domains S1-H1-L1 will interact with the csgD mRNA. Specific mutations were generated within the central element of the pairing interaction, stem H1 (FIG. 7). These disrupted the pseudoknot fold (RydC$_{H1}$), removed its csgD mRNA binding site (RydC$_{H2}$), or restored stem H1 (RydC$_{H3}$). Mutant RydC$_{H1}$ disrupts stem H1 and therefore unfolds the pseudoknot while maintaining its csgD mRNA binding site, resulting in increased efficacy and translation blockage in the absence of Hfq (FIG. 7C). This shows that unfolding the RydC pseudoknot greatly enhances its translational control of csgD mRNA. Mutant RydC$_{H2}$ had a similar effect on CsgD translation, implying that pairings between S1, L1, and the csgD mRNA TIS are necessary and sufficient for translational control. In the regulation triggered by RydC$_{H2}$, in which the pseudoknot was unfolded, the addition of Hfq was not beneficial. Finally, compensatory mutant RydC$_{H3}$ was only half as active as RydC in reducing csgD mRNA translation, and Hfq had no effect on the translation regulation induced by RydC$_{H3}$. Since RydC$_{H3}$ is □ten-fold less active than RydC$_{H1}$ for reducing CsgD translation, it suggests that an unfolded state of the RydC pseudoknot significantly increases its capacity to reduce CsgD translation.

RydC and by Hfq control of the csgD mRNA translation. In vitro translation assays were done to provide direct experimental evidence that RydC, Hfq or an 'RydC-Hfq' complex represses csgD mRNA protein synthesis. These assays were performed on a csgD mRNA$_{503}$ construct encoding the first 119 amino acids of the CsgD protein. Without RydC and Hfq, a 13-kDa polypeptide was detected (FIG. 7C). Hfq reduced CsgD translation down to 40%. This is in agreement with the substantial reduction of the ribosome toeprints induced by Hfq (FIG. 5A, right), and the 20% reduction of translation by RydC (FIG. 7C). When RydC and Hfq acted together, CsgD translation dropped down to 10%. Hfq or elevated amounts of RydC by themselves reduced CsgD translation by impairing ribosome binding, but the presence of an 'Hfq-RydC' complex significantly amplified the regulation. As an internal negative control, similar concentrations of tmRNA did not impact CsgD translation when compared to RydC (FIG. 7C), demonstrating the specificity of the RydC-induced CsgD translation reduction.

Discussion

In the present invention, the inventors show that RydC expression affects biofilm formation and cell adhesion in two enterobacteria: S. enterica and E. coli. RydC is an important negative regulator of curli synthesis in vivo, as its endogenous expression gradually decreases over time while csgD mRNA expression progressively increases and triggers curli synthesis and biofilm formation (FIG. 7D). In addition, the lack of endogenous levels of RydC augments csgD mRNA synthesis (FIG. 3C). This tiny 64 nt-long sRNA also regulates the expression of a membrane transporter involved in nutrient and antibiotic uptake (5,6). E. coli RydC possesses at least two direct targets (yejABEF and csgD mRNAs), which suggests physiological links between these encoded proteins. In Salmonella, RydC regulates bacterial membrane integrity through mRNA stabilization of cyclopropane fatty acid synthase (8). Thus RydC acts both as a target activator/repressor, and as a sensor for nutrient uptake, membrane remodelling, and biofilm formation (FIG. 8A). Interestingly, the RydC pairings with both cfa and csgD mRNAs involve accessible nucleotides at the RydC 5'-end, although in the case of the csgD mRNA, the pairing interaction is longer and spreads deeper into the sRNA pseudoknot. When food supplies are available and enter the bacteria, RydC expression is turned on to enable nutrient uptake and membrane stabilization. It also prevents unwanted biofilm formation, avoiding this survival mode triggered in hostile environments such as under feeding limitations. Previous observations (4) are in agreement with our conclusions, as RydC expression is activated during the exponential growth phase and 'switched off' at the stationary phase. However, when enteric bacteria are in 'curli' and 'biofilm' modes, RydC expression gradually decreases over time (FIG. 7D), probably due to unknown regulators. RydC-induced reduction of biofilm formation and cell adhesion results from a drop-off in curli synthesis via the direct downregulation of CsgD expression at both the RNA and protein levels, which in turn lowers CsgA and CsgB curli structural proteins levels. csgD mRNA is a direct target of RydC and Hfq, reducing translation initiation by blocking the mRNA TIS through direct pairings.

In E. coli, RydC is the sixth Hfq-dependent sRNA that negatively controls CsgD transcription factor expression, and all of these sRNAs impair translation initiation. With the help of Hfq, OmrA, OmrB, RprA, McaS, GcvB, and RydC regulate CsgD expression by pairing at the csgD mRNA 5'-UTR (13-17). Each of these six possesses specific binding sites on the csgD 5'UTR, some with binding overlaps (FIG. 8B). Interestingly, most of the structural changes induced by Hfq on the csgD mRNA overlap with the binding sites of these sRNA regulators (FIG. 8B). Note that Hfq modifies the conformation of the csgD mRNA at and around the binding sites of each of these sRNAs, probably to facilitate pairing between the mRNA target and its RNA regulators. Hfq can, however, repress csgD mRNA translation in the absence of sRNA, as recently observed in the translation inhibition of the cirA mRNA involved in iron uptake (26).

Interestingly, RydC is the only sRNA from the group that pairs exclusively at the csgD mRNA TIS rather than upstream (RprA interacts at both the TIS and upstream). In fact RydC binding still occurred after the removal of 115 nts at the csgD mRNA 5'-end (FIG. 4). In addition, RydC reduces cellular levels of csgD mRNA (FIG. 3), implying that the regulation occurs at both the post-transcriptional and translational levels, as is usually the case for 'Hfq-dependent' sRNAs (27). In bacteria, transcription and translation are simultaneous, but we detected about a 5-hour delay between csgD mRNA and protein synthesis (FIG. 3). This is attributable to previously-reported or unknown regulators of csgD expression acting at the post-transcriptional level. As reported for other sRNAs that interact with Hfq, RydC-Hfq-induced CsgD translation inhibition could promote target mRNA turnover, stimulating endonucleolytic cleavages and decay (28).

The CsgD 5'UTR structure, inferred from structural probes, is highly-folded and includes a portion of the TIS (FIG. 6A). This implies unfolding both when translation initiates and when initiation is blocked through the joint action of Hfq and the six sRNAs that bind at various locations within the csgD 5'UTR (FIG. 8B). In this latter situation, each sRNA acts as a specific external stimulus sensor (FIG. 8A). Hfq facilitates interactions between an sRNA and its targets by binding both RNAs or by restructuring one or both RNAs (3). We previously reported that Hfq binds RydC and restructures its conformation (4), presumably to facilitate pairing with its mRNA targets. Based on previous probing data collected on a RydC-Hfq complex (4), the protein induces reactivity changes at the two connecting single-stranded loops within the RydC pseudoknot, triggering pairing rearrangements within H1. Hfq modifies RydC structure, thus destabilizing H1 (4) but also changing csgD mRNA conformations. These particular RydC domains are those with which our structural and mutational evidence indicates csgD mRNA interacts. Indeed, Hfq interacts with csgD mRNA (FIG. 4C) and reduces its translation in the absence of sRNAs (FIG. 5A). As previously reported for sodB mRNA (28), Hfq remodels both the conformations of RydC and csgD mRNA to improve translational control. In the absence of Hfq, the ribosomal toeprint on the csgD mRNA requires a large amount of RydC (FIG. 5A). Accordingly, CsgD translation decreases only when RydC is in excess (FIG. 7C). Interestingly, RydC is considerably lowered in the presence of Hfq. This implies that Hfq is required in vivo to regulate RydC-induced csgD translation initiation. Hfq orientation and proximity to the complementary target site may facilitate RydC unfolding and the annealing between the two RNAs (29). Hfq could also assist in the exchange of RNA strands between the interacting RNAs.

For the most part, single strands accessible within the scaffolds of sRNAs pair with their mRNA targets, occasionally requiring conformational activations. The interaction between RydC and csgD mRNA is striking because it is the first time that an interaction between an mRNA target and a sRNA pseudoknot, which requires chaperone-induced restricted unfolding, is reported. These observations come from structural and mutational analysis of 'sRNA-mRNA' duplexes, which indicate that the RydC 5'-end is involved in pairings with the csgD mRNA TIS. For pairing, helices H1 from RydC and H7 from the csgD mRNA should unfold. This is probably facilitated by Hfq, which interacts with both RydC (4) and csgD mRNA, to form a ternary complex with the two RNAs (FIG. 4). 5'-seeding between RydC 5'-accessible nucleotides and the csgD mRNA AUG codon is involved in pairing. Demonstrated previously by probing (4), RydC pseudoknot "breathing" in solution opens helix H1 to promote pairing with the csgD mRNA, a transition facilitated by Hfq.

Pseudoknots are ingenious dynamic structural modules that can be temporarily unfolded (here with the assistance of a chaperone) to allow for antisense seed pairing and subsequent propagation. Two pseudoknots have already been detected and experimentally validated in another bacterial sRNA (29). In that case, they both contained an internal open reading frame that can only be translated under specific conditions. Bacterial sRNAs can act as antitoxic components in toxin-antitoxin (TA) systems, and an RNA pseudoknot was recently reported to inhibit and antagonise a harmful protein in the TA pair (30). Antisense RNAs can modulate mRNA pseudoknot formation to control plasmid replication (31), indicating that pseudoknot structural plasticity can also be manipulated by chaperoned RNAs to control gene expression. In addition to their essential roles as cis-regulatory modules within mRNAs (31), including riboswitches (32), regulatory sRNAs pseudoknots are, when assisted by RNA chaperones, ingenious tools for efficient and reversible gene regulation processes in living organisms.

Example 2

The inventors used peptide nucleic acids (PNAs) that hybridize to the CsgD mRNA sequence ranging from nucleic acid at position 128 to nucleic acid at position 151 in SEQ ID NO: 9. In the presence of 20 µM of PNAs corresponding to RydC 1-2tot sequence (SEQ ID NO: 10), *E. coli* biofilm formation was reduced about 50%. The PNAs also present anti-bacterial properties by reducing *E. coli* growth.

Therefore, the inventors provided evidence that the oligonucleotides of the present invention inhibit biofilm formation. The inventors also demonstrated that the oligonucleotides of the present invention inhibit bacterial growth and then represent new anti-bacterial compounds.

REFERENCES

Throughout this application, various references describe the state of the art to which this invention pertains. The disclosures of these references are hereby incorporated by reference into the present disclosure.

1. Storz, G., Vogel, J. and Wassarman, K. M. (2011) Regulation by small RNAs in bacteria: expanding frontiers. *Mol Cell*, 43, 880-891.
2. Sobrero, P. and Valverde, C. (2012) The bacterial protein Hfq: much more than a mere RNA-binding factor. *Crit Rev Microbiol*, 38, 276-299.
3. Soper, T. J., Doxzen, K. and Woodson, S. A. (2011) Major role for mRNA binding and restructuring in sRNA recruitment by Hfq. *RNA*, 17, 1544-1550.
4. Antal, M., Bordeau, V., Douchin, V. and Felden, B. (2005) A small bacterial RNA regulates a putative ABC transporter. *J Biol Chem*, 280, 7901-7908.
5. Novikova, M., Metlitskaya, A., Datsenko, K., Kazakov, T., Kazakov, A., Wanner, B. and Severinov, K. (2007) The *Escherichia coli* Yej transporter is required for the uptake of translation inhibitor microcin C. *J Bacteriol*, 189, 8361-8365.
6. Eswarappa, S. M., Panguluri, K. K., Hensel, M. and Chakravortty, D. (2008) The yejABEF operon of *Salmonella* confers resistance to antimicrobial peptides and contributes to its virulence. *Microbiology*, 154, 666-678.
7. Ortega, A. D., Gonzalo-Asensio, J. and Garcia-del Portillo, F. (2012) Dynamics of *Salmonella* small RNA expression in non-growing bacteria located inside eukaryotic cells. *RNA Biol*, 9, 469-488.
8. Frohlich, K. S., Papenfort, K., Fekete, A. and Vogel, J. (2013) A small RNA activates CFA synthase by isoform-specific mRNA stabilization. *EMBO J*, 32, 2963-2979.
9. Hall-Stoodley, L., Costerton, J. W. and Stoodley, P. (2004) Bacterial biofilms: from the natural environment to infectious diseases. *Nat Rev Microbiol*, 2, 95-108.
10. Romling, U. (2005) Characterization of the rdar morphotype, a multicellular behaviour in Enterobacteriaceae. *Cell Mol Life Sci*, 62, 1234-1246.
11. Ogasawara, H., Yamada, K., Kori, A., Yamamoto, K. and Ishihama, A. (2010) Regulation of the *Escherichia coli* csgD promoter: interplay between five transcription factors. *Microbiology*, 156, 2470-2483.
12. Pesavento, C., Becker, G., Sommerfeldt, N., Possling, A., Tschowri, N., Mehlis, A. and Hengge, R. (2008) Inverse regulatory coordination of motility and curli-mediated adhesion in *Escherichia coli*. *Genes Dev*, 22, 2434-2446.
13. Holmqvist, E., Reimegard, J., Sterk, M., Grantcharova, N., Romling, U. and Wagner, E. G. (2010) Two antisense RNAs target the transcriptional regulator CsgD to inhibit curli synthesis. *EMBO J*, 29, 1840-1850.
14. Thomason, M. K., Fontaine, F., De Lay, N. and Storz, G. (2012) A small RNA that regulates motility and biofilm formation in response to changes in nutrient availability in *Escherichia coli*. *Mol Microbiol*, 84, 17-35.
15. Mika, F., Busse, S., Possling, A., Berkholz, J., Tschowri, N., Sommerfeldt, N., Pruteanu, M. and Hengge, R. (2012) Targeting of csgD by the small regulatory RNA RprA links stationary phase, biofilm formation and cell envelope stress in *Escherichia coli*. *Mol Microbiol*, 84, 51-65.

16. Jorgensen, M. G., Nielsen, J. S., Boysen, A., Franch, T., Moller-Jensen, J. and Valentin-Hansen, P. (2012) Small regulatory RNAs control the multi-cellular adhesive lifestyle of *Escherichia coli*. *Mol Microbiol*, 84, 36-50.

17. Boehm, A. and Vogel, J. (2012) The csgD mRNA as a hub for signal integration via multiple small RNAs. *Mol Microbiol*, 84, 1-5.

18. Kikuchi, T., Mizunoe, Y., Takade, A., Naito, S. and Yoshida, S. (2005) Curli fibers are required for development of biofilm architecture in *Escherichia coli* K-12 and enhance bacterial adherence to human uroepithelial cells. *Microbiol Immunol*, 49, 875-884.

19. Wagner, E. G., Altuvia, S. and Romby, P. (2002) Antisense RNAs in bacteria and their genetic elements. *Adv Genet*, 46, 361-398.

20. Sakellaris, H., Hannink, N. K., Rajakumar, K., Bulach, D., Hunt, M., Sasakawa, C. and Adler, B. (2000) Curli loci of *Shigella* spp. *Infect Immun*, 68, 3780-3783.

21. Barnhart, M. M. and Chapman, M. R. (2006) Curli biogenesis and function. *Annu Rev Microbiol*, 60, 131-147.

22. Collinson, S. K., Clouthier, S. C., Doran, J. L., Banser, P. A. and Kay, W. W. (1996) *Salmonella enteritidis* agfBAC operon encoding thin, aggregative fimbriae. *J Bacteriol*, 178, 662-667.

23. Hammar, M., Arnqvist, A., Bian, Z., Olsen, A. and Normark, S. (1995) Expression of two csg operons is required for production of fibronectin- and congo red-binding curli polymers in *Escherichia coli* K-12. *Mol Microbiol*, 18, 661-670.

24. Hammar, M., Bian, Z. and Normark, S. (1996) Nucleator-dependent intercellular assembly of adhesive curli organelles in *Escherichia coli*. *Proc Natl Acad Sci USA*, 93, 6562-6566.

25. Arnqvist, A., Olsen, A. and Normark, S. (1994) Sigma S-dependent growth-phase induction of the csgBA promoter in *Escherichia coli* can be achieved in vivo by sigma 70 in the absence of the nucleoid-associated protein H-NS. *Mol Microbiol*, 13, 1021-1032.

26. Salvail, H., Caron, M. P., Belanger, J. and Masse, E. (2013) Antagonistic functions between the RNA chaperone Hfq and an sRNA regulate sensitivity to the antibiotic colicin. *EMBO J*, 32, 2764-2778.

27. Gottesman, S. and Storz, G. (2011) Bacterial small RNA regulators: versatile roles and rapidly evolving variations. *Cold Spring Harb Perspect Biol*, 3.

28. Aiba, H. (2007) Mechanism of RNA silencing by Hfq-binding small RNAs. *Curr Opin Microbiol*, 10, 134-139.

29. Panja, S. and Woodson, S. A. (2012) Hfq proximity and orientation controls RNA annealing. *Nucleic Acids Res*, 40, 8690-8697.

30. Sayed, N., Jousselin, A. and Felden, B. (2012) A cis-antisense RNA acts in trans in *Staphylococcus aureus* to control translation of a human cytolytic peptide. *Nat Struct Mol Biol*, 19, 105-112.

31. Brantl, S. (2007) Regulatory mechanisms employed by cis-encoded antisense RNAs. *Curr Opin Microbiol*, 10, 102-109.

32. Babitzke, P., Baker, C. S. and Romeo, T. (2009) Regulation of translation initiation by RNA binding proteins. *Annu Rev Microbiol*, 63, 27-44.

The invention claimed is:

1. An oligonucleotide that hybridizes to a CsgD mRNA sequence ranging from a nucleic acid at position 128 to a nucleic acid at position 151 in SEQ ID NO: 9 and blocks translation of said CsgD mRNA, wherein said oligonucleotide is selected from the group consisting of peptide nucleic acids (PNA), locked nucleic acids (LNA) oligonucleotides, morpholinos oligonucleotides, tricyclo-DNA-antisense oligonucleotides, and U7- or U1-mediated antisense oligonucleotides or conjugate products thereof.

2. The oligonucleotide according to claim 1 which hybridizes to the CsgD mRNA sequence ranging from a nucleic acid at position 128 to a nucleic acid at position 149 in SEQ ID NO: 9.

3. The oligonucleotide according to claim 1 which hybridizes to the CsgD mRNA sequence ranging from a nucleic acid at position 134 to a nucleic acid at position 151 in SEQ ID NO: 9.

4. The oligonucleotide according to claim 1 which comprises or consists of
   i) a nucleic acid sequence ranging from a nucleic acid at position 1 to a nucleic acid at position 24 in SEQ ID NO: 1, a nucleic acid at position 1 to a nucleic acid at position 24 in SEQ ID NO: 2, a nucleic acid at position 1 to a nucleic acid at position 23 in SEQ ID NO: 3, a nucleic acid at position 1 to a nucleic acid at position 24 in SEQ ID NO: 4, a nucleic acid at position 1 to a nucleic acid at position 23 in SEQ ID NO: 5, a nucleic acid at position 1 to a nucleic acid at position 23 in SEQ ID NO: 6, a nucleic acid at position 1 to a nucleic acid at position 21 in SEQ ID NO: 7, a nucleic acid at position 1 to a nucleic acid at position 22 in SEQ ID NO: 8, or a nucleic acid sequence SEQ ID NO: 10, or
   ii) a nucleic acid sequence having at least 70% identity with the nucleic acid sequence ranging from nucleic acid at position 1 to the nucleic acid at position 24 in SEQ ID NO: 1, the nucleic acid at position 1 to the nucleic acid at position 24 in SEQ ID NO: 2, the nucleic acid at position 1 to the nucleic acid at position 23 in SEQ ID NO: 3, the nucleic acid at position 1 to the nucleic acid at position 24 in SEQ ID NO: 4, the nucleic acid at position 1 to the nucleic acid at position 23 in SEQ ID NO: 5, the nucleic acid at position 1 to the nucleic acid at position 23 in SEQ ID NO: 6, the nucleic acid at position 1 to the nucleic acid at position 21 in SEQ ID NO: 7, the nucleic acid at position 1 to the nucleic acid at position 22 in SEQ ID NO: 8, or the nucleic acid sequence SEQ ID NO: 10.

5. A method of inhibiting or reducing bacterial biofilm formation on a surface comprising the step of applying to the surface an amount of an oligonucleotide that hybridizes to a CsgD mRNA sequence ranging from a nucleic acid at position 128 to a nucleic acid at position 151 in SEQ ID NO: 9, wherein the amount is sufficient to block translation of said CsgD mRNA and inhibit or reduce formation of the bacterial biofilm on the surface.

6. A method of preventing or treating biofilm formation in a subject in need thereof comprising the step of administering to the subject an amount of an oligonucleotide that hybridizes to a CsgD mRNA sequence ranging from a nucleic acid at position 128 to a nucleic acid at position 151 in SEQ ID NO: 9, wherein the amount is sufficient to block translation of said CsgD mRNA and prevent or treat formation of the biofilm in the subject.

7. An antimicrobial composition comprising an oligonucleotide that hybridizes to a CsgD mRNA sequence ranging from a nucleic acid at position 128 to a nucleic acid at position 151 in SEQ ID NO: 9, wherein said antimicrobial composition is carried on a material.

8. The antimicrobial composition of claim 7, wherein said material is selected from the group consisting of a sheet, tape, patch, mesh, polymer, fabric, and medical device.

9. An antimicrobial composition comprising an oligonucleotide that hybridizes to a CsgD mRNA sequence ranging from a nucleic acid at position 128 to a nucleic acid at position 151 in SEQ ID NO: 9, wherein said antimicrobial composition is in a form selected from the group consisting of a tablet, gel capsule, powder, granule, and emulsion.

10. An antimicrobial composition comprising an oligonucleotide that hybridizes to a CsgD mRNA sequence ranging from a nucleic acid at position 128 to a nucleic acid at position 151 in SEQ ID NO: 9 and a pharmaceutical carrier selected from the group consisting of lactose, dextrose, sucrose, sorbitol, mannitol, starches, gum acacia, calcium phosphates, alginate, tragacanth, gelatin, calcium silicate, microcrystalline cellulose, polyvinylpyrrolidone, celluose, water syrup, methyl cellulose, methyl and propylhydroxybenzoates, and mineral oil.

11. An antimicrobial composition comprising an oligonucleotide that hybridizes to a CsgD mRNA sequence ranging from a nucleic acid at position 128 to a nucleic acid at position 151 in SEQ ID NO: 9, wherein said oligonucleotide is selected from the group consisting of peptide nucleic acids (PNA), locked nucleic acids (LNA) oligonucleotides, morpholinos oligonucleotides, tricyclo-DNA-antisense oligonucleotides, and U7- or U1-mediated antisense oligonucleotides or conjugate products thereof.

* * * * *